US010717084B2

(12) United States Patent
Sulchek et al.

(10) Patent No.: US 10,717,084 B2
(45) Date of Patent: Jul. 21, 2020

(54) MICROFLUIDIC DEVICES FOR CELLULAR SORTING

(71) Applicant: GEORGIA TECH RESEARCH CORPORATION, Atlanta, GA (US)

(72) Inventors: Todd Sulchek, Atlanta, GA (US); Alexander Alexeev, Atlanta, GA (US); Gonghao Wang, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 202 days.

(21) Appl. No.: 15/774,684

(22) PCT Filed: Nov. 9, 2016

(86) PCT No.: PCT/US2016/061141
§ 371 (c)(1),
(2) Date: May 9, 2018

(87) PCT Pub. No.: WO2017/083391
PCT Pub. Date: May 18, 2017

(65) Prior Publication Data
US 2018/0318837 A1  Nov. 8, 2018

Related U.S. Application Data

(60) Provisional application No. 62/252,709, filed on Nov. 9, 2015.

(51) Int. Cl.
*G01N 33/48* (2006.01)
*G01N 33/00* (2006.01)
(Continued)

(52) U.S. Cl.
CPC .... *B01L 3/502761* (2013.01); *G01N 15/0272* (2013.01); *G01N 33/48* (2013.01);
(Continued)

(58) Field of Classification Search
CPC ............... G01N 33/48; G01N 15/0272; G01N 33/5005; B01L 3/502761
See application file for complete search history.

(56) References Cited

U.S. PATENT DOCUMENTS

| 8,356,714 B2 | 1/2013 | Sulchek et al. |
| 2011/0003303 A1* | 1/2011 | Pagano ................. B03C 1/0332 435/6.19 |

(Continued)

OTHER PUBLICATIONS

International Search Report and Written Opinion from PCT Application No. PCT/US16/61141 dated Feb. 15, 2017 (11 pages).
(Continued)

*Primary Examiner* — Brian J. Sines
(74) *Attorney, Agent, or Firm* — Troutman Sanders LLP; Ryan A. Schneider

(57) ABSTRACT

Microfluidic devices for cell sorting or cell fractionation are disclosed. A microfluidic device can comprise one or more inlets, a first wall and a second wall, and two or more outlets. The first and second walls can be substantially planar to each other and the first wall having can have a plurality of ridges protruding from the first wall and defining a compression gap between the ridge and a surface of the second wall. The microfluidic device can also be a cell sorting device for sorting a plurality of cells based on one or more biophysical cellular properties including size, elasticity, viscosity, and/or viscoelasticity wherein the cells are subjected to one or more compressions due to the compression gap. Also disclosed are methods for cell sorting based on a variety of biophysical cellular properties.

23 Claims, 15 Drawing Sheets

(51) Int. Cl.
  *G01N 15/06* (2006.01)
  *B01L 3/00* (2006.01)
  *G01N 15/02* (2006.01)
  *G01N 33/50* (2006.01)
  *G01N 15/00* (2006.01)
  *G01N 33/49* (2006.01)

(52) U.S. Cl.
  CPC .... *G01N 33/5005* (2013.01); *B01L 3/502776* (2013.01); *B01L 2200/0652* (2013.01); *B01L 2300/0816* (2013.01); *B01L 2300/0864* (2013.01); *B01L 2400/086* (2013.01); *G01N 33/491* (2013.01); *G01N 2015/0065* (2013.01); *G01N 2015/0288* (2013.01)

(56) References Cited

U.S. PATENT DOCUMENTS

| | | | |
|---|---|---|---|
| 2011/0081674 A1* | 4/2011 | Han | C12M 47/04 435/29 |
| 2014/0227777 A1* | 8/2014 | Choi | B01L 3/502761 435/309.1 |
| 2014/0230909 A1* | 8/2014 | Di Carlo | B01L 3/502707 137/2 |
| 2015/0226657 A1* | 8/2015 | Foster | G01N 15/10 435/287.1 |
| 2015/0246353 A1* | 9/2015 | Arai | G01N 33/491 435/2 |
| 2016/0303565 A1* | 10/2016 | Bhagat | G01N 15/0255 |
| 2017/0122937 A1* | 5/2017 | Arai | G01N 33/54313 |

OTHER PUBLICATIONS

Wang, G., et al., "Stiffness Dependent Separation of Cells in a Microfluidic Device," PLOS One, vol. 8, No. 10 Oct. 15, 2013.
Choi, S., et al., "Hydrophoretic High-Throughout Selection of Platelets in Physiological Shear-Stress Range," Lab on a Chip, vol. 11 Feb. 7, 2011.
Mao, W., "Hydrodynamic Sorting of Microparticles by Size in Rigid Microchannels," Physics of Fluids vol. 23 May 19, 2011.

\* cited by examiner

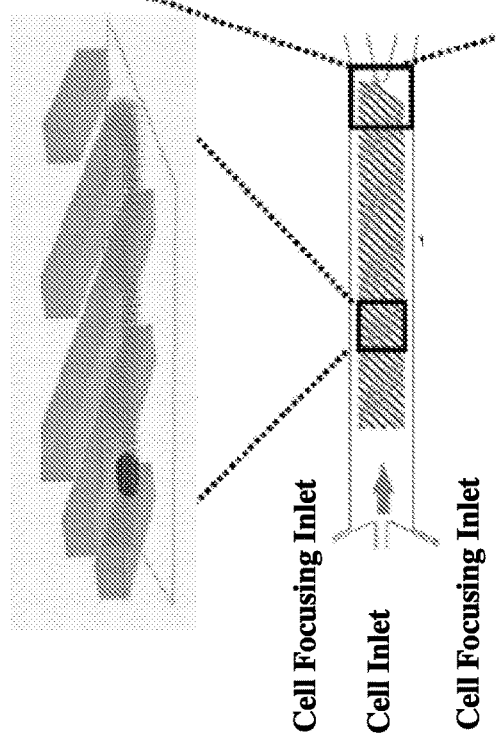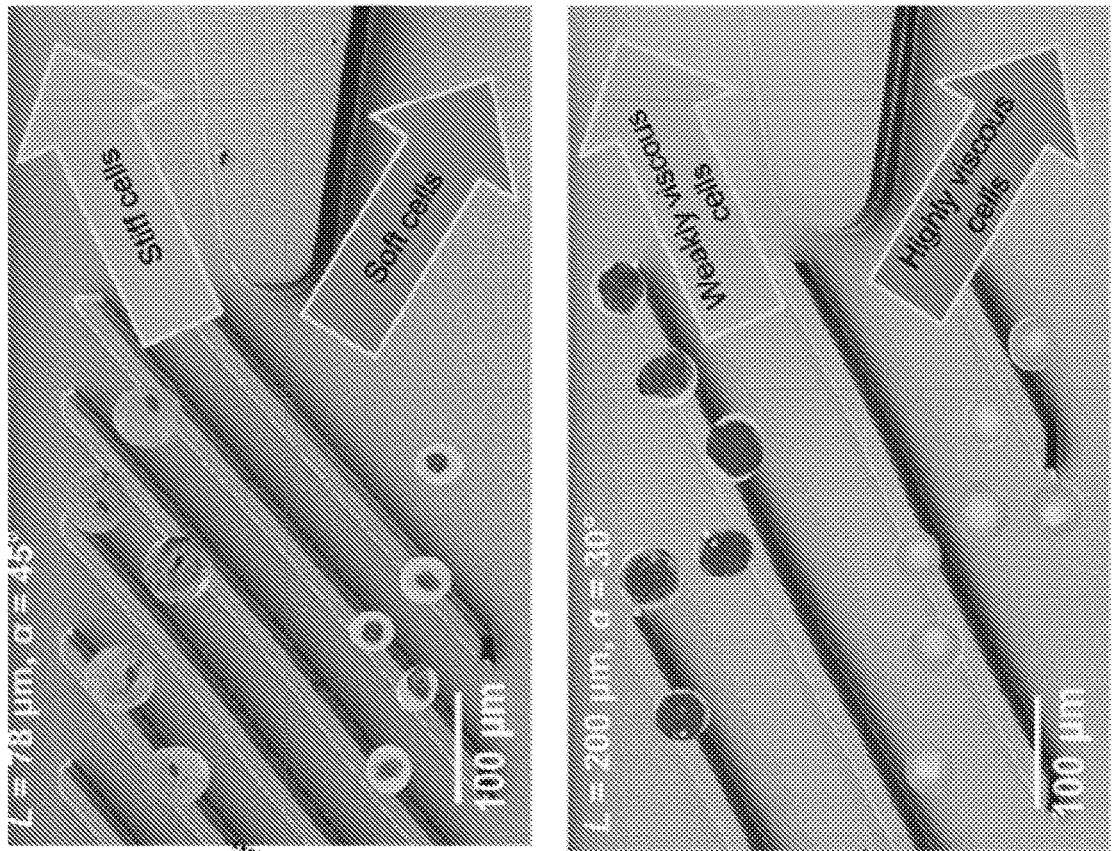
FIG. 1b

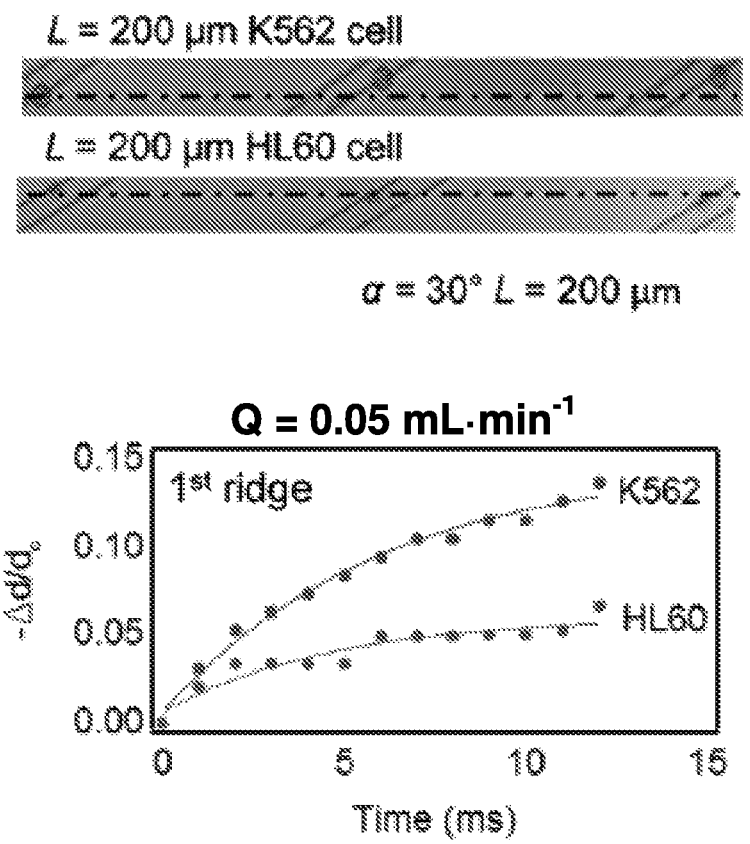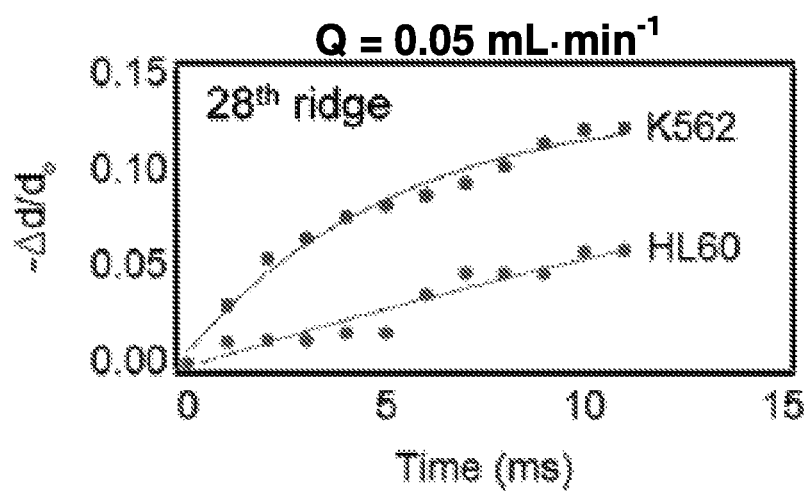
FIG. 4d

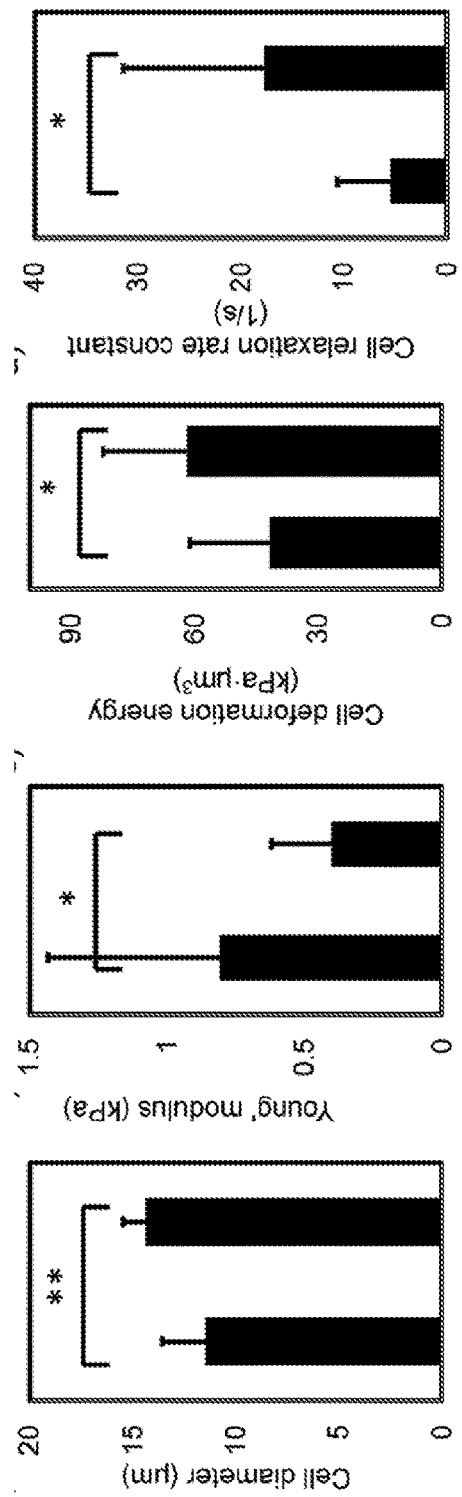
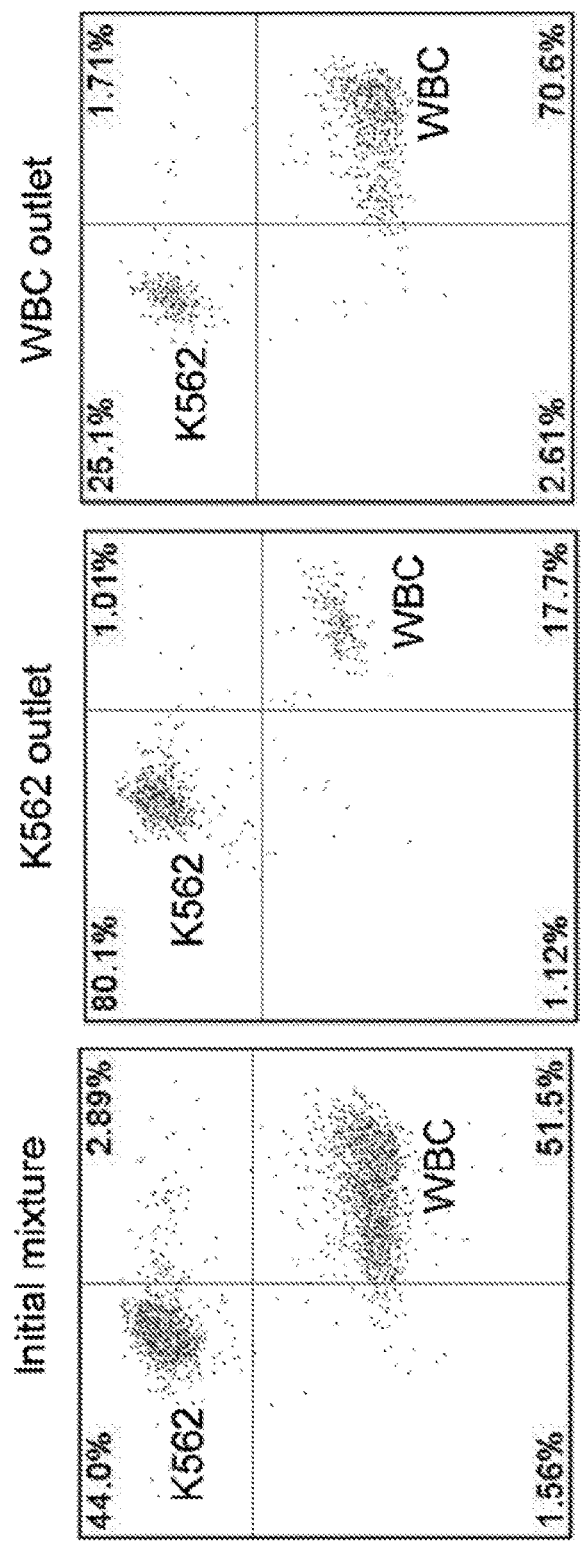

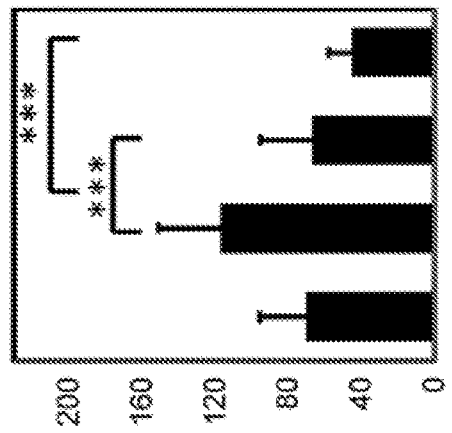
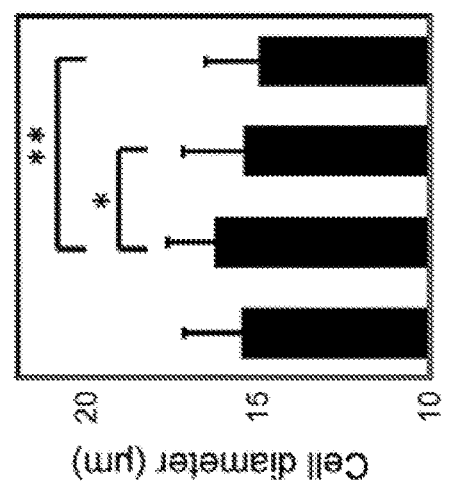
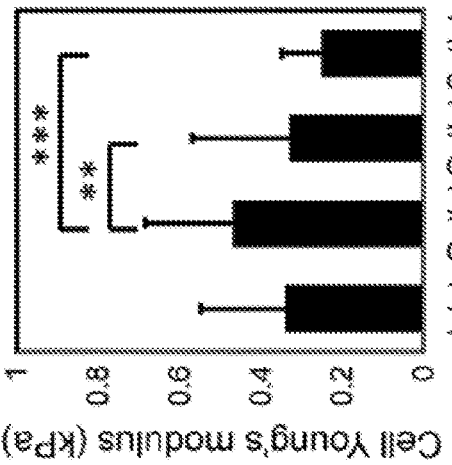
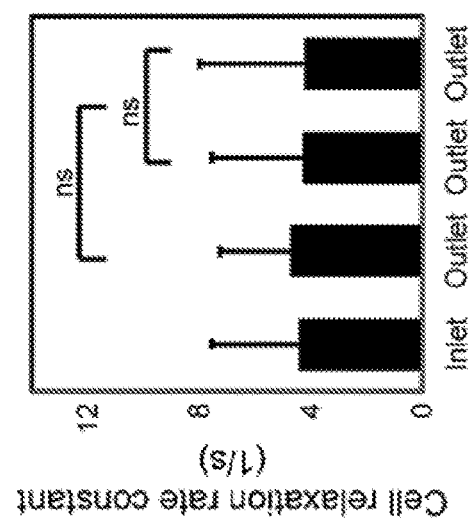
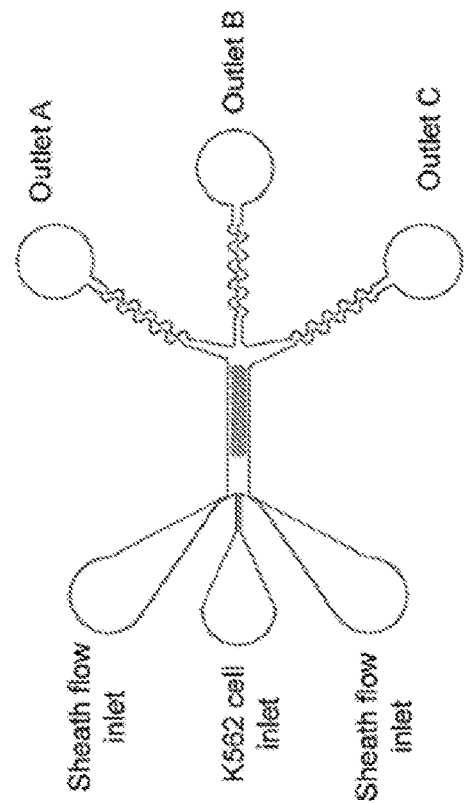

MICROFLUIDIC DEVICES FOR CELLULAR SORTING

CROSS-REFERENCE TO RELATED APPLICATIONS

This application is a U.S. National Stage Entry of PCT/US2016/061141, filed on Nov. 9, 2016, which claims the benefit of U.S. Provisional Patent Application No. 62/252,709, filed Nov. 9, 2015, entitled "Microfluidic Device for Biophysical Fractionation of Cells and Particles," the entire contents and substance of each of which are hereby incorporated by reference as if fully set forth below.

STATEMENT OF FEDERALLY SPONSORED RESEARCH

This invention was made with government support under grant number CBET0932510 awarded by the National Science Foundation. The government has certain rights in the invention.

TECHNICAL FIELD

The various embodiments of the disclosure relate generally to processes, methods, and systems for cellular sorting. It is particularly useful for cell sorting based on a variety of biophysical properties and biomechanical properties, including elasticity, viscosity, and viscoelasticity, and high purity cell sorting.

BACKGROUND

In recent years, the links between disease states, cell function, and cell biophysical properties have been actively studied in a variety of pathologies, including cancer, malaria, and sickle cell anemia. Although determining biophysical properties of cells is currently employed in clinical care, particularly differences in cell density and size, utilizing new biophysical markers in conjunction with existing biochemical and biomolecular assays has the potential to greatly increase the sensitivity and specificity of detecting target cells.

Viscoelasticity is a biophysical property of cells that exhibits both elastic (reaction to deformation) and viscous (reaction to the rate of deformation) properties after undergoing stress and deformation. Viscoelasticity is a very important property of cells undergoing any dynamic process, such as the deformation of blood cells during circulatory flow. For example, changes in the ability of blood cells to deform and relax can result in severe complications. Whereas healthy leukocytes and erythrocytes deform when passing through capillaries and restore to their original shape after exit, highly viscous and stiffer leukemia cells, caused from altered cytoplasmic composition and enlarged nucleus, result in increased blood flow resistance. Variation in elasticity and viscosity of the red blood cells also affects the microcirculatory blood flow, which results in diminished ability to transport oxygen in sickle cells patients. Therefore, sorting and enriching cells by viscoelastic properties has tremendous clinical value.

Cell separation is also vital in several clinical diagnostic applications such as detection of cancer and infectious diseases. In hospitals and laboratories, cell separation is routinely carried out by centrifugation, size exclusion, and cell sorters based on fluorescent signals. The demand to obtain high-purity cell population at low cost spurred growing interest in exploring alternative cell separation methods based on microfluidics. For example, electric fields can be used to separate cells in microfluidic channels based on cell surface charge distribution. Magnetic fields can be used to separate cells with different surface proteins that bind magnetic particles in microfluidic channels. Also, acoustic fields can be used to separate cells of different sizes. In addition, research studies have shown that cell biomechanical properties including size and stiffness are biomarkers of diseases such as cancer and malaria. The changes in cell biomechanical properties are attributed to the transformation of cellular structures such as the cytoskeleton and nucleus. Therefore, cell biomechanical properties are phenotypes that could potentially be used for clinical diagnostics and therapies. Several recent studies have used hydrodynamic force and optical force to distinguish cell phenotypes based on cell mechanical properties.

Utilizing differences in cell biomechanical properties for disease detection would be greatly aided by means to sort cells biomechanically. Biomechanical properties are intrinsic to the cell and as such provide a label-free approach to enrichment without the need to discover and develop biomolecular reagents to aid detection. In addition, microfluidic platforms enable continuous sample processing, improve sensitivity, and utilize small sample volume. Recently, several microfluidic cell sorting approaches based on variations in cell biomechanical properties have been demonstrated. However, the ultimate purity of the separated cells is limited by the intrinsic variability and overlap of the biomechanical properties of different cell types, even if the average properties are substantially different. As a result, biomechanical approaches to cell enrichment are in general inferior to the best results achieved by cell sorting methods based on antibody binding of magnetic or fluorescent signals.

BRIEF SUMMARY

The various embodiments of the disclosure relate generally to processes, methods, and systems for cell sorting using microfluidic devices An embodiment of the disclosure can be a microfluidic device comprising a first wall and a second wall, the walls being substantially planar to each other, and the first wall having a plurality of ridges. The plurality of ridges can be diagonally oriented with respect to a central axis of the microfluidic device and each respective ridge of the plurality of ridges can be separated by a ridge spacing. Each ridge of the plurality of ridges can protrude normal to the first wall and define a compression gap between the ridge and a surface of the second wall. The compression gap can have a height that is about 4 to about 16 microns, about 5 to about 14 microns, or about 6 to about 11 microns. Each ridge of the plurality of diagonally-oriented ridges can form a ridge angle with respect to the central axis of the microfluidic device. The ridge angle can be about from about 20 to about 70 degrees, about 30 degrees, about 45 degrees, or about 60 degrees. Additionally, the microfluidic device can comprise at least 7 ridges, but may comprise 7 to 21 ridges, or 14 ridges.

Each respective ridge of the plurality of ridges can be separated by a ridge spacing. The ridge spacing can have a width that can be about 50 to about 350 microns or about 100 to about 300 microns. In some embodiments, the width of the ridge spacing is about 100 to about 200 microns and a ridge angle formed by at least one ridge with respect to the central axis of the microfluidic device is about 30 degrees. In some embodiments, width of the ridge spacing is about 100 microns or less and a ridge angle formed by at least one ridge with respect to the central axis of the microfluidic device is about 45 degrees. In some embodiments, the width of the ridge spacing is about 200 microns, a ridge angle formed by at least one ridge with respect to the central axis of the microfluidic device is about 30 degrees, and the plurality of ridges comprises 30 ridges.

The microfluidic device can comprise one or more inlets and two or more outlets. In some embodiments, the microfluidic device may comprise three outlets. The microfluidic device can also comprise an expansion region downstream from the plurality of ridges. At least one outlet of the microfluidic device can comprise a flow apportionment region, a flow balancing region, and a collection point. In some embodiments, at least one flow apportionment region can have a different size than at least a second flow apportionment region. In some embodiments, at least one flow balancing region can comprise a serpentine channel.

An embodiment of the disclosed microfluidic device can be a cell sorting device for sorting a plurality of cells based on one or more biophysical cellular properties including size, elasticity, viscosity, and/or viscoelasticity. The cell sorting device can comprise an inlet for flowing a cell medium comprising the plurality of cells into the device at a flow velocity, a plurality of outlets for collecting sorted portions of the plurality of cells, and a top planar wall and a bottom planar wall. The top planar wall can comprise a plurality of ridges protruding normal to the top planar wall and defining a compression gap between a surface of the bottom planar wall and each ridge of the plurality of ridges. Additionally, each ridge of the plurality of ridges can be oriented diagonally with respect to a central flow axis and each respective ridge of the plurality of ridges can be separated by a diagonally-oriented ridge spacing. Embodiments of the cell sorting device can comprise some or all of the aspects discussed above with respect to the microfluidic device.

In addition to the inlet, the cell sorting device can also comprise one or more sheath flow inlets. The sheath flow inlets can be used for flowing a sheath fluid into the cell sorting device and provide a focus cell inlet.

The cell sorting device can comprise a plurality of outlets for collecting sorted portions of the plurality of cells wherein the sorted portions share one or more biophysical properties. When sorting based on viscosity or viscoelasticity, the cell medium can comprise at least a first cell portion that is more viscous than at least a second cell portion. The more viscous cell portion can follow a different trajectory than the less viscous cell portion due to one or more of the plurality of compression gaps, the ridge spacing, the number of ridges, the ridge angle, and the flow velocity. The cell sorting device can sort the more viscous cells from the less viscous cell portion and collect the sorted portions in each outlet of the plurality of outlets. The compression gap, therefore, can comprise a height smaller than the average diameter of the plurality of cells flowed through the device and the plurality of cells can go through one or more compressions.

An embodiment of the present disclosure comprises a method for sorting a plurality of cells including providing a cell medium, the cell medium comprising a plurality of cells to be sorted, passing the cell medium through a microchannel having a plurality of diagonally-oriented ridges, and collecting sorted portions of the cell medium at two or more collection points. The plurality of diagonally-oriented ridges can define a compression gap between a bottom surface of the microchannel and each ridge of the plurality of ridges. Additionally, when the cell medium passes through the microchannel, at least a portion of the plurality of cells can undergo one or more compressions due to the compression gap. Each respective ridge of the plurality of diagonally-oriented ridges can also be separated by a diagonally-oriented ridge spacing. The method can have some or all of the features discussed above with respect to the microfluidic device and the cell sorting device.

The microchannel can comprise at least two trajectories for the plurality of cells at each ridge. In some embodiments, the trajectories can be determined by a characteristic of the cell selected from cell size, stiffness, relaxation time, viscosity, or elasticity, and combinations thereof. In some embodiments, the cell medium can comprise at least a first cell portion that is more viscous than at least a second cell portion and the more viscous cells can be collected at a first collection point and the less viscous cell portion can be collected at a second collection point. Additionally, the cell medium can be provided to the microfluidic device at a flow velocity of about 3 to about 1000 mm/s.

BRIEF DESCRIPTION OF THE DRAWINGS

FIG. 1b a diagram of a cell sorting device and images showing one or more cell mixtures infused into a microfluidic channel of a cell sorting device, in accordance with an exemplary embodiment of the present disclosure

FIGS. 4c and 4d compare the cell relaxation of two cell types in a microfluidic device with a ridge spacing of L=100 µm and L=200 µm, in accordance with an exemplary embodiment of the present disclosure.

FIGS. 6A-6d compare the cell diameter, Young's modulus, cell deformation energy, and cell relaxation constant for WBC and K562 cell types, in accordance with embodiments of the present disclosure.

FIG. 6e shows a flow cytometric analysis of cell enrichment for an embodiment having a ridge angle of 30 degrees, a ridge spacing of 200 µm, and a ridge count of 30 ridges, in accordance with embodiments of the present disclosure FIGS. 7a-7e compare the cell diameter, Young's modulus, cell deformation energy, and cell relaxation constant for two different cell types in a three-outlet microfluidic device, in accordance with embodiments of the present disclosure.

FIGS. 8a-8e show an AFM comparison of cells sorted based on cell diameter, Young's modulus, cell deformation energy, and cell relaxation, in accordance with embodiments of the present disclosure

DETAILED DESCRIPTION

Figure 1A:
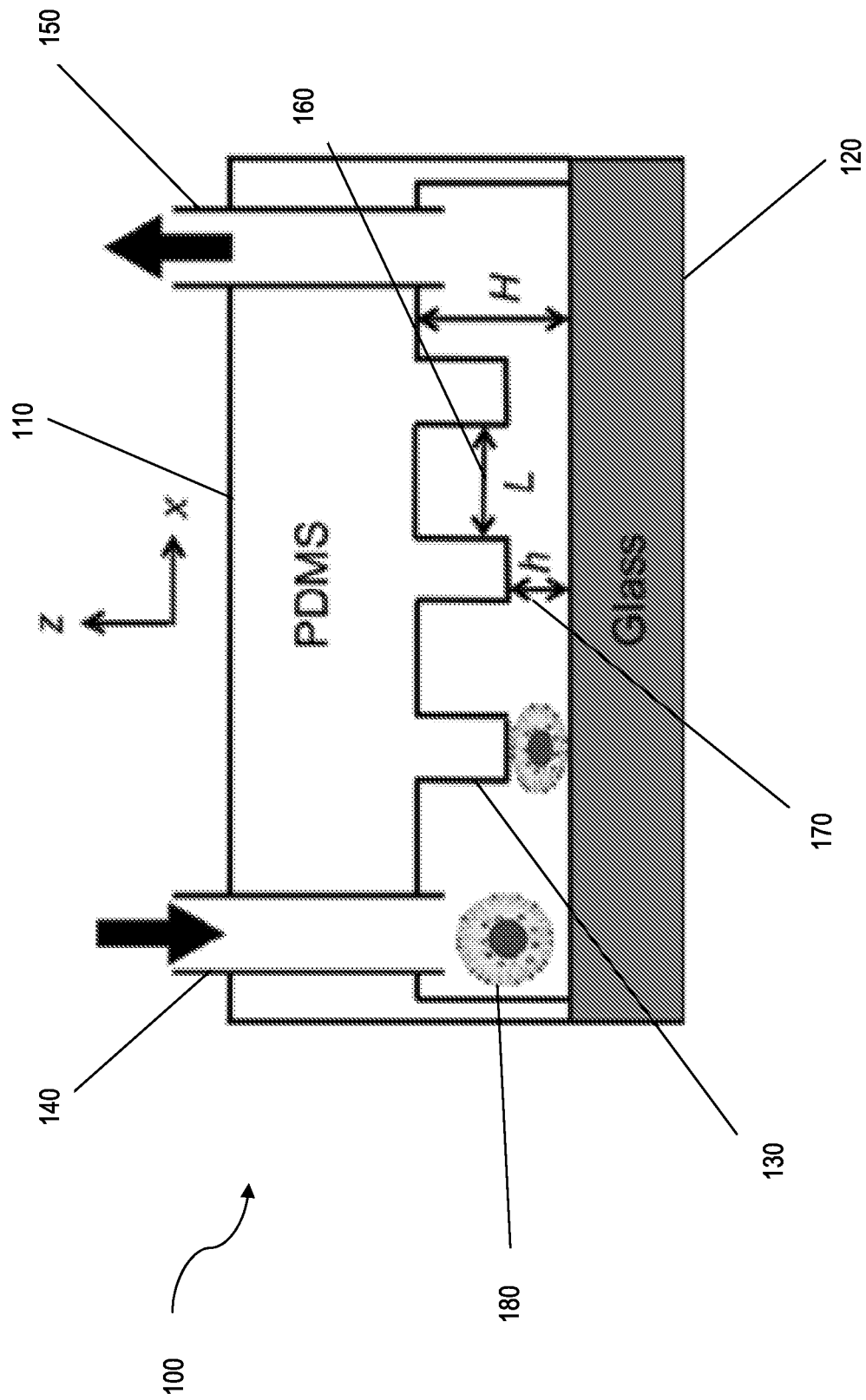
FIG. 1a is a cross-sectional diagram of a cell sorting device, in accordance with an exemplary embodiment of the present disclosure.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Microfluidic devices for use in cell sorting are disclosed. In some embodiments, the microfluidic device can sort a plurality of cells based on a variety of biophysical and biomechanical properties, including size, viscosity, elasticity, and viscoelasticity. For example, in an embodiment for cell sorting based on viscoelasticity, the microfluidic device can sort or separate cells into highly viscous and weakly viscous portions. In an exemplary embodiment, the disclosed microfluidic devices can comprise a plurality of ridges that are diagonally oriented. Additionally, the disclosed microfluidic devices can comprise a plurality of compression gaps for constricting the one or more cells and influencing the trajectory of cells as they progress through the microfluidic device. Depending on one or more biophysical or biomechanical properties, cells can progress through the microfluidic device following a unique trajectory. In some embodiments, the microfluidic device can comprise an increased number of outlets that can separate cells into groups having a higher purity.

Various microfluidic devices are described. The described microfluidic devices can comprise a microchannel defined by a first planar wall and a second planar wall. The microchannel may comprise a plurality of ridges protruding outwardly from a planar wall. The ridge can protrude perpendicularly (i.e. normal) from one or both of the planar walls, but does not necessarily need to. The plurality of ridges can protrude from one of the first planar wall or the second planar wall. For instance, each of the plurality of ridges can protrude outwardly from the first planar wall and towards a second planar wall. In some embodiments, the plurality of ridges can protrude outwardly from both the first planar wall and the second planar wall. For example, each of the plurality of ridges can protrude outwardly from the first planar wall towards a second plurality of ridges protruding outwardly from the second planar wall.

The microfluidic device may comprise a plurality of diagonally-oriented ridges. For instance, the one or more ridges may be diagonally-oriented with respect to a central axis of the microfluidic device. The central axis may comprise an axis extending parallel to the first planar wall and the second planar wall. The plurality of diagonally-oriented ridges can extend parallel to each subsequent ridge of the plurality of ridges. The plurality of diagonally-oriented ridges may be straight, but need not be. Additionally, the plurality of diagonally-oriented ridges can be any shape, including but not limited to rectangular, cylindrical, trapezoidal, or triangular.

The microfluidic device can be defined by one or more geometric parameters of the microfluidic device that can be changed as desired. For instance, the plurality of ridges can define a compression gap, a ridge spacing, a ridge angle, the number of ridges, a channel length, and a ridge thickness. As used herein, the dimensions of the respective elements each reflect an average measurement of the element in the device.

Disclosed are a plurality of ridges that may define a compression gap between a ridge and a surface of an opposing planar wall. For instance, in an embodiment wherein the plurality of ridges protrudes from the first planar wall, the plurality of ridges may define a compression gap between a ridge and a surface across from the ridge on the second planar wall. As used herein, a surface may include the closest or nearest portion of the opposing wall, for example where the wall does not otherwise have corresponding ridges or protrusions. In some embodiments the second planar wall can comprise a plurality of ridges, and the opposing surface can be, for example, an opposing ridge. The compression gap can therefore be defined as the space formed between a ridge and a surface of the second wall, or the space between opposing ridges on opposing walls. Typically, the opposing ridges will be aligned with each other as well. The size of the compression gap can be increased or decreased as desired, based on device design. In some embodiments, the height of the compression gap may be from about 4 to about 16 microns, from about 5 to about 15 microns, from about 5 to about 14, from about 6 to about 14, from about 6 to about 12, or from about 6 to about 11 microns.

The plurality of ridges may be separated by a ridge spacing. The ridge spacing can include the channel or gap formed between respective ridges. The ridge spacing may be increased or decreased as desired, based on device design. In some embodiments, the ridge spacing may be from about 50 to about 1000 microns, from about 50 to about 750 microns, from about 50 to about 500 microns, from about 50 to about 400 microns, from about 50 to about 350 microns, from about 100 to about 300 microns, from about 100 to about 750 microns, from about 100 to about 500 microns, from about 100 to about 400 microns, from about 100 to about 300 microns, about 100 to about 250 microns, or from about 125 to about 250 microns. The ridge spacing can be at least about 50 microns, at least about 100 microns, at least about 125 microns, at least about 150 microns, at least about 250 microns, or at least about 300 microns. The ridge spacing can be up to about 5 microns, up to about 3 microns, up to about 2 microns, up to about 1 microns, up to about 750 microns, or up to about 500 microns.

The diagonal orientation of the plurality of ridges with respect to the central axis can be defined by a ridge angle. The ridge angle (α) and the central axis, i.e. the flow direction, can be seen for example in FIG. 1b. The ridge angle may be increased or decreased, based on device design. For instance, in some embodiments, the ridge angle can be from about 20 to about 75 degrees, at least about 30 degrees, at least about 45 degrees, or at least about 60 degrees. The ridge angle of each respective ridge may also be the same or different along a length of the microfluidic device. In instances where a ridge is not linear, the angle can be measured based on a line that is a linear fit to the non-linear ridge.

The number of ridges in the microfluidic channel can be increased or decreased as desired. In some embodiments, the microfluidic device can comprise 5 to 100 ridges. In some embodiments, the microfluidic device can comprise at least 3 ridges, at least 4 ridges, at least 5 ridges, at least 6 ridges, at least 7 ridges, at least 8 ridges, at least 9 ridges, or at least 10 ridges. In some embodiments, the microfluidic device can comprise up to 100 ridges, up to 75 ridges, up to 50 ridges, or up to 40 ridges. In some embodiments, the microfluidic device can include 5 to 50 ridges, 7 to 40 ridges, or 7 to 21 ridges. In some embodiments, the microfluidic device can comprise about 14 ridges.

The plurality of ridges can be described by a ridge thickness. The ridge thickness can be defined as the linear measurement of the ridge in the direction of primary flow. The ridge thickness can be increased or decreased as desired, based on device design. In some embodiments, the ridge thickness can be from about 7 to about 30 microns, from about 7 to about 20 microns, from about 7 to about 18 microns, from about 7 to about 16 microns, from about 7 to about 11 microns, from about 7 to about 9 microns, from about 20 to about 30 microns, from about 22 to about 28 microns, from about 24 to about 28 microns, from about 18 to about 21 microns, from about 16 to about 22 microns, or from about 8 to about 11 microns. In some embodiments the ridge thickness can be at least about 9 microns, at least about 11 microns, and at least about 16 microns.

The microfluidic device can have one or more inlets. The one or more inlets may be located on a first side wall of the microfluidic device. In some embodiments, the microfluidic device can have a cell inlet and a sheath flow inlet. In some embodiments, the cell inlet can be located between a first sheath flow inlet and a second sheath flow inlet, or can be surrounded by a first sheath flow inlet. In some embodiments, the cell inlet can be downstream from one or more sheath flow inlets, or can be aligned with one or more sheath flow inlets.

The microfluidic device may comprise two or more outlets. In some embodiments, the microfluidic device can comprise at least two outlets, at least three outlets, at least four outlets or at least five outlets. The number of outlets can be two, three, four or five.

The described microfluidic devices can be constructed in a variety of ways. In one exemplary non-limiting embodiment, the microfluidic devices can be made using a replica molding of polydimethylsiloxane (PDMS) on a permanent mold. The mold can be created by two-step photolithography patterning of a photoresist on a 4-inch-diameter silicon wafer. After the removal of PDMS from the mold, inlet and outlet holes can be punched in the side walls of the PDMS, and the PDMS can be subsequently bonded to a glass substrate to form the microfluidic channel.

Embodiments of the microfluidic device may be used for sorting a plurality of cells (i.e. a cell sorting device) based on one or more biophysical or biomechanical properties, including but not limited to, size, elasticity, viscosity, and/or viscoelasticity. Cell sorting device may comprise some or all of the features discussed above. An exemplary microfluidic device for cell sorting 100 is illustrated in FIGS. 1a and 1b. The cell sorting device 100 can comprise a top planar wall 110 and a bottom planar wall 120. The top planar wall 110 can comprise a plurality of ridges 130 protruding outwardly from the top planar wall 110. The cell sorting device 100 can comprise one or more inlets 140 provided for flowing one or more of a cell medium comprising a plurality of cells 180 and a sheath flow fluid into the cell sorting device 100. The cell sorting device 100 can comprise a plurality of outlets 150 for collecting sorted portions of the plurality of cells 180 wherein the sorted portions may share one or more biophysical properties. Top planar wall 110 and bottom planar wall 120 are shown as being made of PDMS and glass, respectively, but are not so limited and can be made of any material known to one of ordinary skill.

The cell sorting device can comprise a plurality of ridges 130 wherein the ridges are diagonally-oriented with respect to a central flow axis, as illustrated at FIG. 1b. The central flow axis can be located proximate a central portion of the cell sorting device and comprise an axis running parallel to a primary flow through the cell sorting device. Each ridge of the plurality of ridges 130 can have a ridge thickness that is at least about the average diameter of the cells flowed through the cell sorting device, and as discussed previous. Each ridge of the plurality of ridges 130 can define a compression gap 170, as discussed above. The compression gap 170 can be formed between a ridge 130 and a surface of the bottom planar wall 120. As will be understood, the plurality of cells that are flowed through the cell sorting device can go through a state of compression and a state of relaxation due to the compression gap 170, and as illustrated at FIG. 1a.

Each compression gap 170 can be sized smaller than the average diameter of a cell, or in other words, as a function of the size of the cell. For example, in an embodiment where the cell medium flowed through the cell sorting device comprises T-cells having an average diameter of 9 microns, the compression gap can have a height between 5 and 7 microns. For example, in an embodiment where the cell medium flowed through the cell sorting device comprises stem cells having an average diameter of 16 microns, the compression gap can have a height between 8 and 10 microns. For example, in an embodiment where the cell medium flowed through the cell sorting device comprises B-cells having an average diameter of 11 microns, the compression gap can have a height between 6 and 8 microns. In some embodiments, the compression gap can have a diameter that is between about 30% to about 85% of the diameter of the cells flowed through the cell sorting device, about 40% to about 80% of the diameter of the cells flowed through the cell sorting device, or about 50% to about 75% of the diameter of the cells flowed through the cell sorting device.

The plurality of ridges may be separated by a ridge spacing 160. The ridge spacing 160 can comprise the width of a space or channel formed between a first ridge of the plurality of ridges and a second ridge of the plurality of ridges. In some embodiments, the ridge spacing 160 may be from 50 to about 1000 microns, from about 50 to about 750 microns, from about 50 to about 500 microns, from about 50 to about 400 microns, from about 50 to about 350 microns, from about 100 to about 300 microns, from about 100 to about 750 microns, from about 100 to about 500 microns, from about 100 to about 400 microns, from about 100 to about 300 microns, about 100 to about 250 microns, or from about 125 to about 250 microns. The ridge spacing can be at least about 50 microns, at least about 100 microns, at least about 125 microns, at least about 150 microns, at least about 250 microns, or at least about 300 microns. The ridge spacing can be up to about 5 microns, up to about 3 microns, up to about 2 microns, up to about 1 microns, up to about 750 microns, or up to about 500 microns, about 50 to about 350 microns, from about 100 to about 300 microns, from about 100 to about 250 microns, from about 125 to about 250 microns, or at least 300 microns. Adjusting the ridge spacing 160 can permit cell sorting by different cellular properties. In an embodiment for cell sorting based on viscoelasticity, increasing the spacing between the ridges can be advantageous because it allows for increased relaxation time for less viscous cells so they can be sorted from highly viscous cells.

The plurality of ridges may comprise a ridge angle (α), as illustrated at FIG. 1*b*. The plurality of ridges 130 can be inclined at an angle to create hydrodynamic circulations underneath the ridge and can be designed to compress and translate cells normal to the flow direction. The ridge angle can also affect the trajectories of cells. The ridge angle may vary depending on one or more parameters including, but not limited to, the types of cells flowed through the cell sorting device, the ridge spacing, and the flow velocity of the medium flowed through the cell sorting device. As such, adjusting the ridge angle may facilitate migration of cells along the ridges, particularly when the cells are less viscous. For instance, increasing the ridge angle may permit a longer relaxation time for less viscous cells before the less viscous cells are subjected to a subsequent compression gap. In other words, the ridge angle may influence the trajectory of a cell and in turn the sorting capabilities of the cell sorting device.

The cell medium can be flowed into the cell sorting device at a flow velocity. The flow velocity can be increased or decreased as desired, based on device design. As used herein, the flow velocity can describe the velocity of the cell medium at an inlet or at an outlet. The flow velocity can be from about 3 to about 1000 mm/s, from about 3 to about 500 mm/s, from about 3 to about 250 mm/s, from about 3 to about 100 mm/s, from about 3 to about 50 mm/s, from about 3 to about 25 mm/s. The flow velocity can be at least about 3 mm/s, at least about 20 mm/s, at least about 50 mm/s, at least about 100 mm/s, or at least about 500 mm/s. The flow velocity can be about 3 mm/s, about 20 mm/s, about 500 mm/s, or about 1000 mm/s. The flow velocity can also be adjusted as a function of the length of the channel, and/or the size of the ridge spacing, based on device design. For instance, increasing the length of the channel can allow for a greater flow velocity. Increasing the velocity in similarly sized devices can result in increased pressure within the device. By increasing the length of the device, the increased pressure can be accounted for while permitting higher flow velocity. Increasing the size of the ridge spacing can permit for greater positive lateral displacement in cells having certain biophysical properties (such as increased stiffness or viscosity). For instance, increasing the ridge spacing can permit increasing the flow velocity as the greater space allows the cells a longer distance over which to travel and be subjected to secondary flow in the ridge channels. As such, increased ridge spacing can permit an increased relaxation time and positive lateral displacement for certain cells despite greater flow velocity.

In some embodiments, and as illustrated at FIG. 1*b*, the cell sorting device can comprise one or more sheath flow inlets (or cell focusing inlets) for flowing a sheath fluid into the cell sorting device. A sheath fluid can allow for hydrodynamic focusing of the cell medium. The one or more sheath flow inlets can be located proximate the cell flow inlet, or upstream of the cell flow inlet. Focusing the cells in the inlet can comprise providing a sheath fluid to the sheath flow inlet until the sheath fluid reaches laminar flow and then subsequently introducing the cell medium cell medium through the cell inlet. The cells can be introduced into the cell inlet by injection, for example by syringe pumps.

When a cell medium is flowed through the microfluidic device, cells, depending on one or more biophysical or biomechanical properties, may follow unique trajectories. The trajectories can be determined by the biophysical or biomechanical properties or characteristic of the cell selected from cell size, stiffness, relaxation time, viscosity, or elasticity, and combinations thereof. For instance, as illustrated at FIG. 1*b*, after flowing through a compression gap, less viscous cells may have a longer relaxation time before flowing beneath a subsequent compression gap. As such, less viscous cells may be more susceptible to secondary flow within the channels formed between each respective ridge. For instance, after a less viscous cell is subjected to compression by the compression gap, the less viscous cell may follow secondary flow within the ridge channels and therefore show greater lateral displacement down the ridge channels compared to more viscous cells. Therefore, the less viscous cells may follow a unique trajectory from the more viscous cells.

The cell sorting device can comprise a plurality of outlets for collecting sorted portions of the plurality of cells wherein the sorted portions share one or more biophysical or biomechanical properties. For instance, in an embodiment sorting cells based on viscoelasticity, the cell sorting device can comprise two outlets wherein one outlet collects highly viscous cells and the second outlet collects less viscous cells. As discussed above, cells having different biophysical or biomechanical properties may follow unique trajectories, e.g. cells may travel through the device towards a particular outlet based on one or more biophysical or biomechanical properties. As will be understood, increasing the outlets can result in more focused sorting with increased purity.

The disclosed microfluidic devices, as described above, can also be used for high purity cell sorting based on a variety of biomechanical properties. For instance, the microfluidic device can sort a plurality of cells based on one or more of cell stiffness (i.e. cell elasticity), cell viscosity, and cell size. In embodiments for cell sorting based on stiffness, viscosity, and/or cell size, the number of outlets can be increased to provide for greater purity in cell sorting. Multiple outlets can be advantageous in some instances as these outlets can provide for finer gradation of cells based on cell biomechanical properties compared to the binary outputs.

Figure 2A:
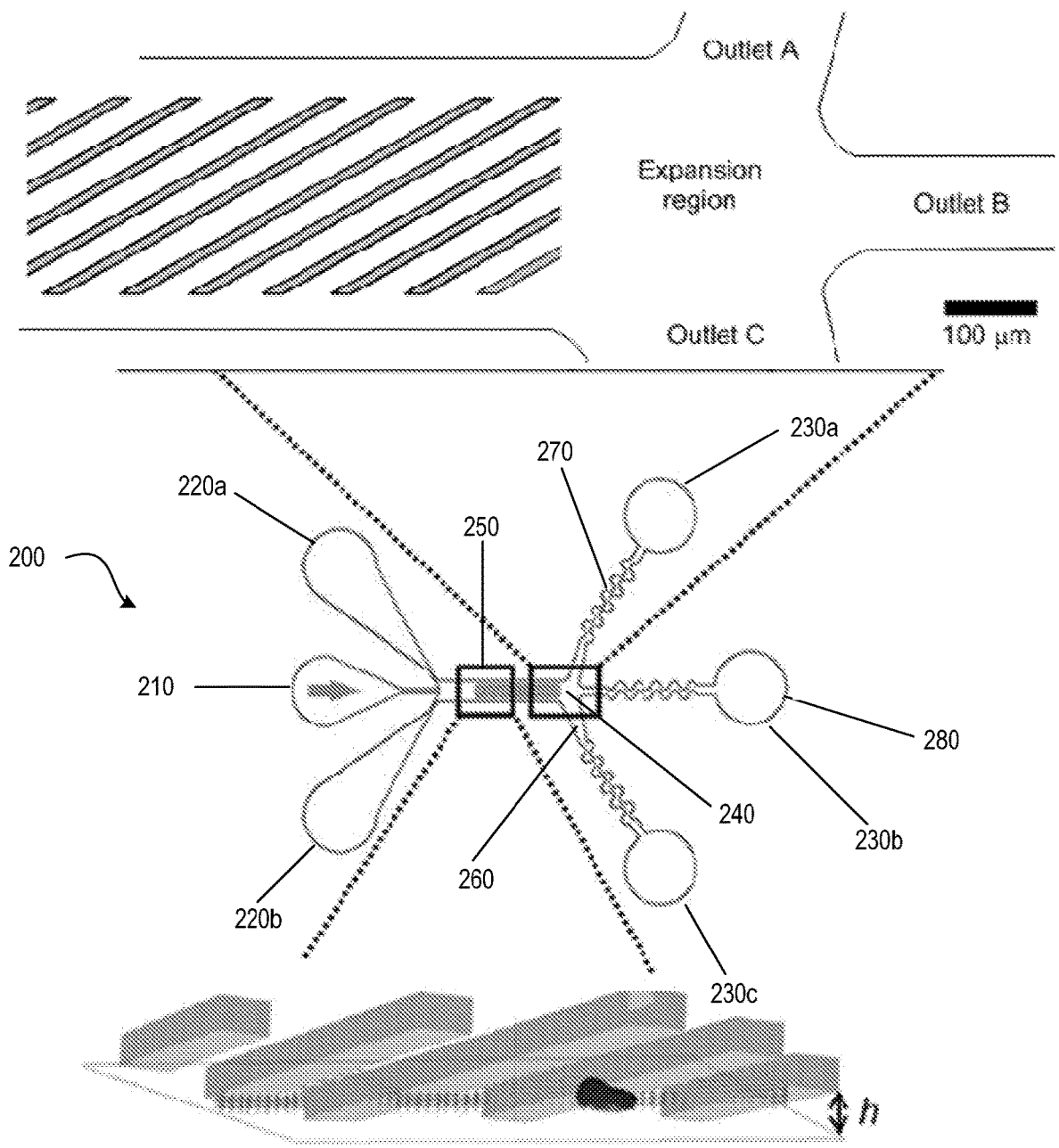
FIG. 2a is a schematic showing a three-outlet, microfluidic cell sorting device having a plurality of diagonal ridges, in accordance with an exemplary embodiment of the present disclosure.
Figure 2B:
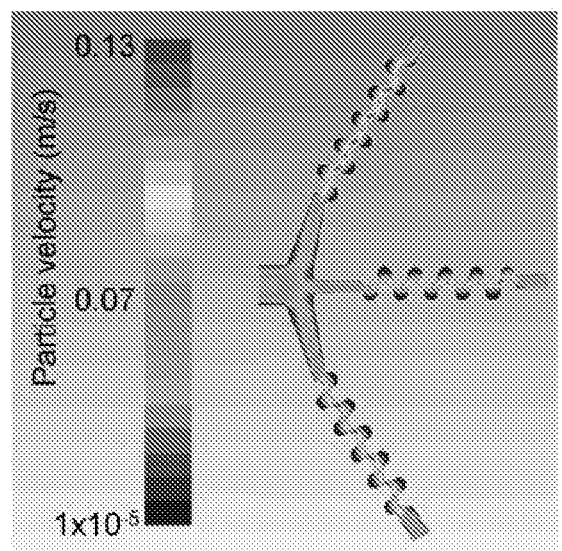
FIG. 2b shows various computational fluid dynamics simulations used to engineer hydrodynamic balancing near the outlets, in accordance with an exemplary embodiment of the present disclosure.
Figure 2C:
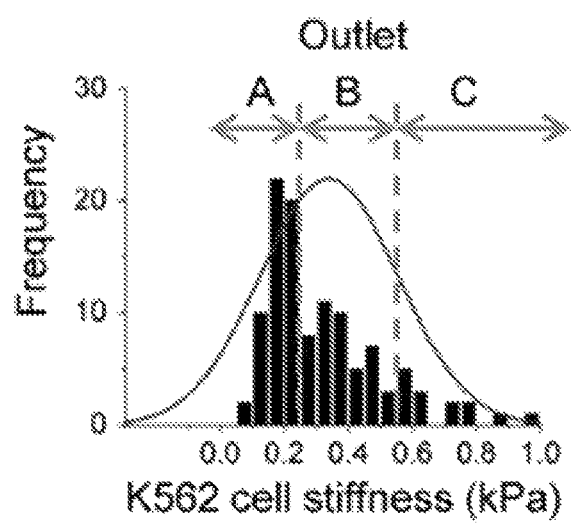
FIG. 2c shows a schematic describing cell fractionation of a single cell type (K562) based on the spread of cell stiffness, in accordance with an exemplary embodiment of the present disclosure.
Figure 2D:
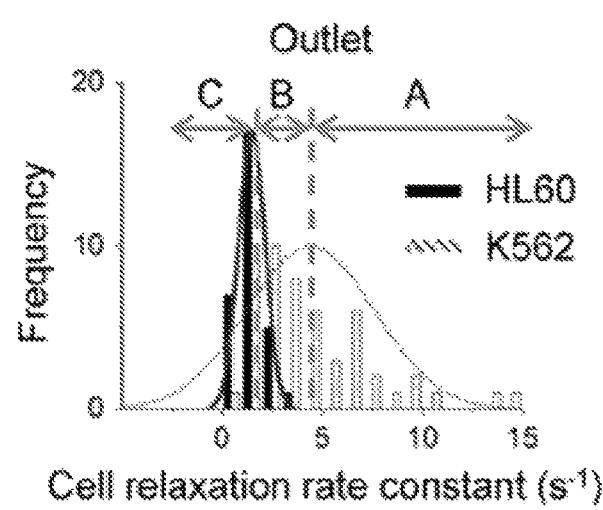
FIG. 2d shows a schematic describing cell fractionation of two cell types (K562 and HL60) based on the spread of cell relaxation, in accordance with an exemplary embodiment of the present disclosure.

For example, FIG. 2a illustrates a non-limiting example of a microfluidic device 200 can comprising three outlets (230a, 230b, 230c). The microfluidic device 200 can comprise, for example, a top outlet 230a, a central outlet 230b, and a bottom outlet 230c. The central outlet 230b can be configured to collect cells that have moderate biomechanical properties. For instance, in the case of separation of two cell types, the central outlet 230b can collect those cells that have overlapping or moderate biomechanical properties, as illustrated at FIG. 2c. As a result, the cells collected at the top 230a and bottom 230b outlets can have pronouncedly different biomechanical properties, as illustrated at FIG. 2d.

The disclosed microfluidic devices may comprise an expansion region and a plurality of hydrodynamically balanced outlets. FIG. 2a illustrates an exemplary and non-limiting three-outlet microfluidic device 200 comprising an expansion region 240 and three hydrodynamically balanced outlets (230a, 230b, 230c). The hydrodynamically balanced outlets (230a, 230b, 230c) can each independently comprise a flow apportionment region 260, a flow balancing region 270, and a collection point 280. The expansion region 240 can comprise a ridge-free portion of the microfluidic channel 250 comprising the plurality of ridges. The expansion region 240 can be in fluid communication with the flow apportionment regions 260 of the outlets (230a, 230b, 230c). The expansion region 240 and flow apportionment regions 260 can have an added benefit of evenly dividing channel flow amongst the outlets (230a, 230b, 230c). In some embodiments, at least one of the outlets can comprise a flow apportionment region that is larger or smaller than at least a flow apportionment region of another outlet. In a non-limiting example, as illustrated at FIG. 2a, the flow apportionment region of the bottom outlet 230c is larger than the flow apportionment region of the top outlet 230a and the bottom outlet 230b.

The outlets (230a, 230b, 230c) may also each independently comprise a flow balancing region 270 and a collection point 280. The flow balancing region 270 can be downstream from and in fluid communication with the flow apportionment region 260. The collection point 280 can be downstream from and in fluid communication with the flow balancing region 270. The flow balancing region 270 can be designed so as to increase the flow resistance in the outlet and prevent flow biasing from uneven flow apportionment regions and external perturbations. The optimal architecture of the expansion region 240, flow apportionment regions 260, and flow balancing regions 270 can be determined using computational fluid dynamics to design a balanced channel flow egress across all outlets, as illustrated at FIG. 2b. In a non-limiting example, and as illustrated at FIG. 2a, the flow balancing regions 270 can comprise a substantially serpentine architecture. As will be understood, the flow balancing region can comprise a variety of shapes, architectures, and lengths depending on the device design.

In view of the disclosed device described above, the disclosure can also include methods for sorting a plurality of cells using a microfluidic device as described above. A cell medium may be provided to a microfluidic device, as described above, and sorted using the microfluidic device. The method can include sorting a plurality of cells using the microfluidic device, the method including the steps of providing a cell medium, the cell medium comprising the plurality of the cells to be sorted, passing the cell medium through a microchannel having a plurality of diagonally-oriented ridges; and collecting sorted portions of the cell medium at two or more collection points. As discussed above, the plurality of diagonally-oriented ridges can define a compression gap between a bottom surface of the microchannel and each ridge of the plurality of ridges. When the cell medium passes through the microchannel, at least a portion of the plurality of cells undergo one or more compressions at the compression gaps.

The method can include collecting the cell medium at two collection points, three collection points, at least three collection points, or more than three collection points, as further disclosed above. The method includes at least two different trajectories for the plurality of cells at each ridge. The cells can pass along the ridge in the space between two ridges, or the cells can pass under the ridge by undergoing compression at the compression gap. A certain portion of the cells can pass along each of these trajectories, as discussed above and exemplified in the examples below. The trajectories can be determined by certain cellular characteristics. Those characteristics can include cell size, stiffness, relaxation time, viscosity, or elasticity, and combinations thereof. In particular, the cellular characteristic can include viscosity and/or elasticity, or viscosity. In an embodiment, the cell medium can include at least a first cell portion that is more viscous than at least a second cell portion. The more viscous cells can be collected at a first collection point and the less viscous cell portion can be collected at a second collection point.

In some embodiments, the cells undergo a compression in the method of about 25 to 85% of the average diameter of the cells, about 30% to about 85% of the diameter of the cells, about 40% to about 80% of the diameter of the cells, or about 50% to about 75% of the diameter of the cells flowed through the cell sorting device.

Other aspects of the method can be reflected in the disclosure set forth above. The cell medium can be provided to the microfluidic device at a flow velocity as disclosed above. The respective ridges of the plurality of diagonally-oriented ridges can be separated by a diagonally-oriented ridge spacing, as defined above. The ridge angle in the device formed with respect to a central flow axis can be as described above. The compression gap can be smaller than the average cell diameter of the cell flowing through the device, and can be at heights as described above. The plurality of diagonally-oriented ridges can include from at least 5 to 100 or more ridges, and can be as defined above. And the method can be operated in a device that includes expansion regions, a flow balancing region and a flow apportionment region, as described above. Each of the device elements set forth above and expanded below are incorporated here in the method as well.

EXAMPLES

Example 1—Device for Cell Sorting Based on Viscoelasticity

Designing Microfluidic Channels for Sorting Based on Viscoelasticity

The parameters defining the microfluidic channel can be determined using computational fluid dynamics Cell dynamic mechanical response to compression can be divided into two components characterized by a storage modulus (elastic, G') and a loss modulus (viscous, G"). Since the channel ridges can compress all cells to the same size, differences in cell size result in different amounts of deformation. To account for differences in cell size, cells can be characterized by a parameter related to cell deformation energy to group the cell elasticity and cell size into size-adjusted elasticity. In this manner, the cell elasticity can be normalized with respect to cell size. A time-independent Young's modulus and cell diameter can be applied to represent elastic modulus and cell size respectively. To determine the elastic deformation energy, the Hertzian contact mechanics model can be applied in which the equivalent elastic modulus $E^*$ as set forth in Equation 1 (Eq. 1). Where $v$ is the Poisson's ratio and $E$ is the Young's modulus.

$$\frac{1}{E^*} = \frac{1 - v_{cell}^2}{E_{cell}} + \frac{1 - v_{channel}^2}{E_{channel}} \quad \text{(Eq. 1)}$$

Modeling the deformed cell as an elastic sphere, the deformation energy, U, representing size-adjusted elasticity, can be derived by integrating the compression force, F, over the cell deformation S as set forth in Equation 2 (Eq. 2), where S is the amount of deformation of a compressed cell, estimated as the difference between cell diameter, d, and ridge gap, h. As a result, the deformation energy can incorporate both cell elasticity and cell size.

$$U = \int F dS = \int \frac{4}{3} E * \left(\frac{d}{2}\right)^{0.5} (S)^{1.5} dS \quad \text{(Eq. 2)}$$

A model was created to relate the biophysical properties to cell trajectory in the microfluidic cell sorter. The model describing the cell trajectory in the microfluidic channel depends on three factors: the size-adjusted elasticity (cell deformation energy), the cell viscosity, and the strength of the secondary flow, which is represented by the ratio of non-axial volumetric flow to axial volumetric flow. The size-adjusted elasticity and viscosity are biophysical properties of the cell. The strength of the helical secondary flow is controlled by the channel geometry and flow rate. As a result of these factors, cell trajectory under the ridge mostly depends on the cell biophysical properties while cell trajectory in between ridges is controlled by the strength of the secondary flow.

Since the cells are viscoelastic, their dynamic response after compression is time-dependent. Experiments show that cell relaxation depends not only on a short time scale characterizing sequential compressions but also on a longer time scales due to mechanical changes within cells resulting from repeated compressions. It was assumed that the viscoelastic response of cells can vary over the course of repeated cell compression events in the cell sorting microchannel.

Differences in cell viscosity can be exploited by engineering ridge geometry and spacing to take advantage of cell relaxation. As a cell initially confronts the ridge, it resists deformation through positive lateral displacement while squeezing through the gap space. However after compression, a highly viscous cell remains deformed, while a weakly viscous cell relaxes more fully before entering a subsequent ridge. Therefore, we can expect that the trajectory of the highly viscous cells is primarily dominated by the secondary flow while less viscous cells are dominated by the deformation energy due to the compressions. Consequently, if the ridge spacing is expanded to allow the cell sufficient time to relax and to restore the original undeformed shape, the trajectory of a highly viscous cell will again be similar to a weakly viscous cell. A microfluidic device can be designed using these principles.

Fabrication of Microfluidic Channels

Microfluidic channels with periodic slanted ridges were fabricated by permanently bonding molded polydimethylsiloxane (PDMS, Sylgard 184, Dow Corning) to a glass substrate. The microfluidic channel features were formed by replica molding of PDMS on a reusable SU-8 mold (SU-8 2007, Microchem Corp.) formed using two-step photolithography on a four-inch diameter silicon wafer. PDMS base and a curing agent were mixed at 10:1 ratio and poured directly onto the SU-8 mold. After degassing, the PDMS was cured at 60 degree Celsius for 6 hours. After curing, the PDMS was removed from the SU-8 mold and the inlet and outlet holes were punched, along with other features of the microfluidic channels. Prior to bonding, the microfluidic feature dimensions were measured with 3D laser confocal microscopy technique (LEXT Olympus). PDMS was treated with air plasma (PDC-32G Harrick) and bonded to a glass slide to form the microfluidic channel After bonding, the channel was incubated at 60 degree Celsius for an hour. To prevent non-specific cell adhesion to the microfluidic channel walls, the microfluidic channel was primed with bovine serum albumin (Sigma Aldrich) at concentration of 10 mg per mL and incubated at 4 degree Celsius overnight.

Materials and Flow Experiment Setup

K562 cells (CCL-243) and HL60 cells (CCL-240) were purchased from ATCC. K562 and HL60 cells were cultured and maintained in Iscove's modified Dulbecco's medium (ATCC) with the addition of 10% fetal bovine serum (FBS). Cells were stored at 37 degree Celsius with 5% $CO_2$. Cells were expanded to 0.5 million cells per mL in a culture flask over two days. Whole blood was withdrawn from healthy donors. White blood cells were separated from fresh whole blood using Ficoll-Paque (1.077, GE Life Sciences) through centrifugation. The remaining red blood cells were lysed using red blood cell lysis buffer for human (Alfa Aesar). The isolated white blood cells were from 1 to 2 million cells per mL of whole blood and were resuspended in DPBS. For characterization of sorting by flow cytometric analysis (Accuri C6, BD), cells were labeled with lipid stains (Bybrand, Life Technologies) at 5 uL reagent per mL of cell suspension.

Cell mixtures at concentration from 1 to 2 million cells per mL were contained in a 3 mL syringe and infused into the microfluidic channel using syringe pumps (PHD 2000, Harvard Apparatus) at controlled flow rates. The cell trajectories were observed by mounting the microfluidic chip on an inverted microscope (Eclipse Ti, Nikon) and recorded by high-speed camera (Phantom v7.3, Vision Research) at a frame rate of 2000 frames per second. The high-speed videos were analyzed with a customized algorithm in ImageJ to extract cell trajectories.

Cell stiffness and relaxation rate data were measured using an atomic force microscope (AFM, MFP-3D, Asylum Research). All cells were measured with a rounded cell shape to closely resemble the morphology within the microfluidic channel. A monolayer of poly-L-lysine (MW 300 k, Sigma Aldrich) to serve as anchors to slightly attach cells to the glass substrate to improve cell stability during AFM measurement. The cell stiffness was represented by the average young's modulus. Beaded silicon nitride cantilevers (spring constant 37.1 pN per nm) were used to indent the center of cells at 1.5 µm per second. Sufficient force was applied to achieve at least 4 µm deformations such that it was in close comparison with our microfluidic compression. Each cell was characterized by three force-indentation curves and fit to a Hertzian model to compute the average Young's modulus. The cell viscosity was characterized by the relaxation rate constant. After maximum indentation of the cell, the tip was held in place while the compression force was monitored for 10 seconds so that cell relaxation can be measured. Cell relaxation was fit to an exponential function and the relaxation rate constant of the cell was calculated.

Cell Biophysical Properties of HL60 and K562 Cells

Figure 3A:
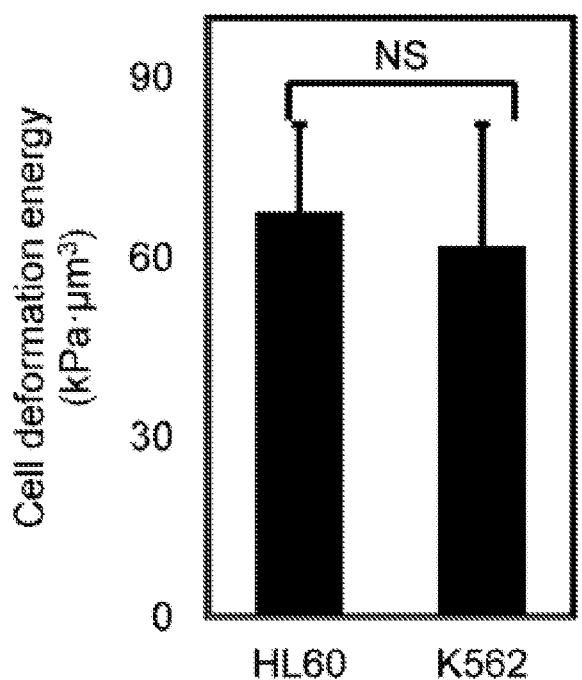
FIGS. 3a-3d compare the cell diameter, Young's modulus, cell deformation energy, and cell relaxation constant of HL60 and K562 cells, in accordance with an exemplary embodiment of the present disclosure.
Figure 3B:
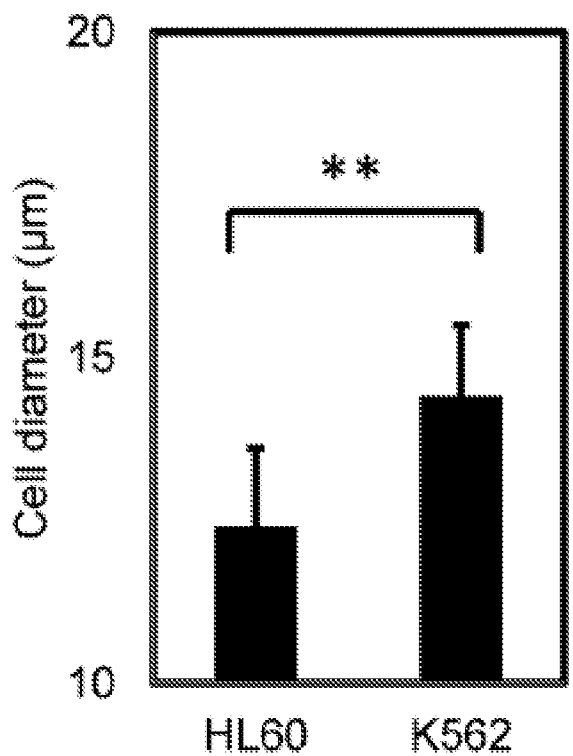
Figure 3C:
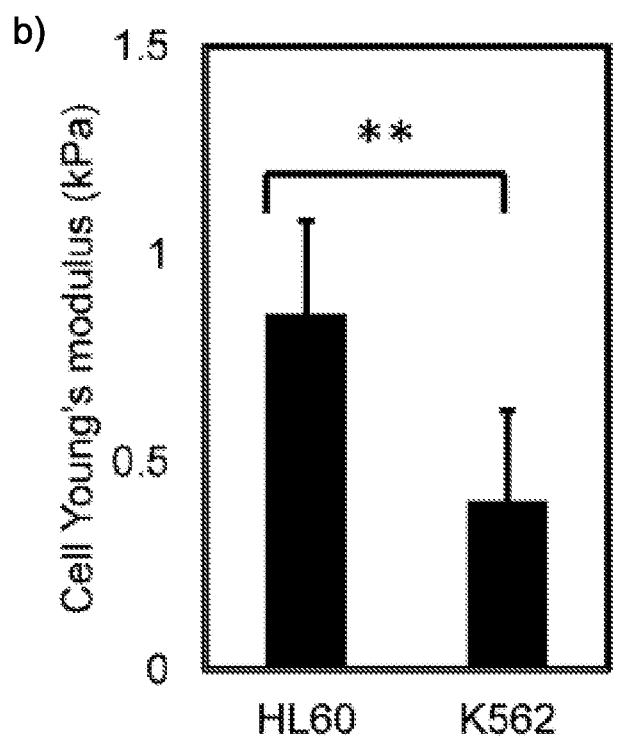
Figure 3D:
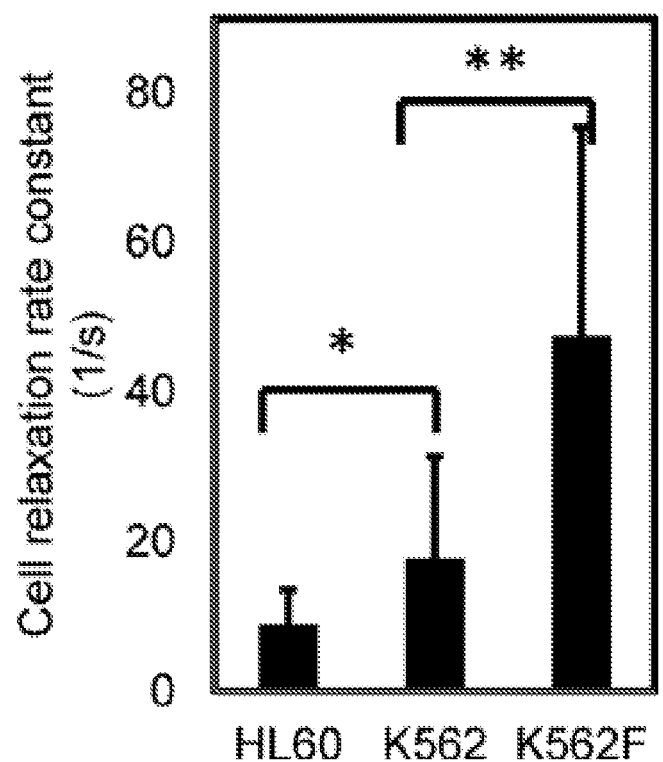

Two leukemia cell lines, K562 and HL60, were selected to demonstrate microfluidic sorting of cells based on differences in cell viscosity. These two cell types have differences in cell size (FIG. 3a) and cell elasticity (FIG. 3b), yet exhibit similar size-adjusted elasticity (deformation energy) (FIG. 3c). The cell relaxation rate measured with AFM indicated the K562 cells were less viscous compared to HL60 cells (FIG. 3d).

Effect of Channel on Lateral Displacement

Figure 4A:
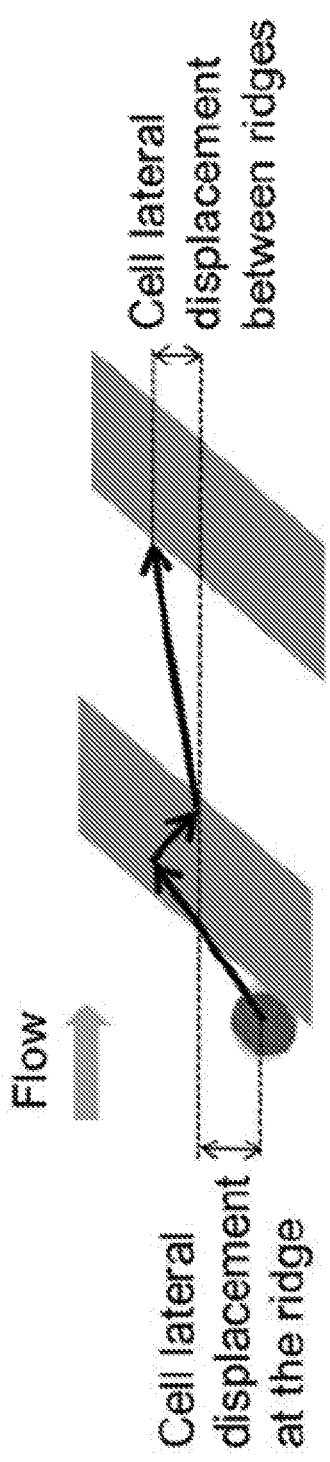
FIGS. 4a and 4b compare the cell lateral displacement between ridges and map the trajectory of weakly viscous cells versus highly viscous cells, in accordance with an exemplary embodiment of the present disclosure.
Figure 4B:
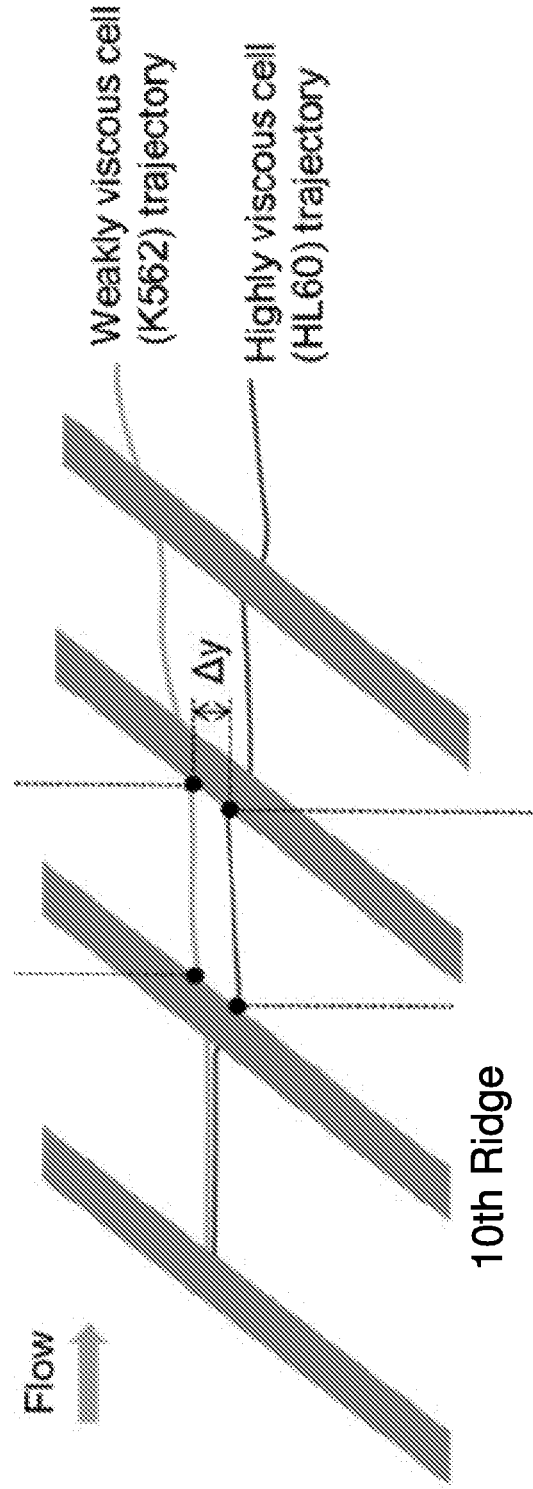

The lateral cell trajectory within the microfluidic channel can be composed of two segments: lateral displacement at the ridge and lateral displacement between the ridges (FIG. 4a). At the ridge, the lateral displacement mainly depends upon the cell biophysical properties since the cell body must deform to squeeze through the space between the ridge and bottom substrate. The lateral displacement at the ridge has at least two components. Depending on the cell stiffness, resistance to deformation by the leading edge of the ridge may cause call movement either along the ridge or perpendicular to the ridge. When cells completely reside underneath the ridge, they move perpendicular to the ridge in response to the flow field regardless of the biophysical properties because the compression is complete. As such the cell lateral displacement can be characterized by the total displacement at the ridge as the cells touch the leading edge of the ridge and immediately after the cells completely exit the ridge. In between the ridges, the lateral displacement depends on the strength of the circulation induced by the ridge. The circulation generated by the ridges results in positive cell lateral displacement independent of cell viscoelastic properties (FIG. 4b).

Channel Parameters

Several geometric parameters of the channel were examined to determine their effect including: compression gap size (h), ridge angle ($\alpha$), ridge spacing (L), and number of compressions. The magnitude of the secondary flow increases with increasing ratio of the ridge height and channel height. All channels used the same channel height (H=20 µm), thus the smaller gap size results in stronger secondary flow. The effect of magnitude of the secondary flow on cell trajectory is not significantly for HL60 and K562 cells as the lateral displacement between ridges did not differ as evidenced in Table 1. As a consequence, the secondary flow is not a major contributing factor to cell separation.

TABLE 1

| K562 cell lateral displacement per ridge (µm) | | | | | |
| --- | --- | --- | --- | --- | --- |
| Channel design | 1st ridge | 10th ridge | 28th ridge | 68th ridge | Between ridge |
| 30° ridge (L = 100 µm) | 0.89 ± −23 | 6.04 ± 2.80 | −6.08 ± 2.86 | −7.95 ± 2.58 | 7.42 ± 1.36 |
| 45° ridge (L = 78 µm) | 0.31 ± 0.067 | −5.88 ± 2.74 | −5.94 ± 2.60 | N/A | 7.08 ± 1.29 |
| 30° ridge (L = 200 µm) | 0.91 ± 0.34 | −3.56 ± 2.31 | −5.61 ± 2.41 | N/A | 10.1 ± 0.9 |

| HL60 cell lateral displacement per ridge (µm) | | | | | |
| --- | --- | --- | --- | --- | --- |
| Channel design | 1st ridge | 10th ridge | 28th ridge | 68th ridge | Between ridge |
| 30° ridge (L = 100 µm) | −4.03 ± 0.94 | −11.1 ± 2.44 | −11.4 ± 1.83 | −12.1 ± 1.58 | 7.87 ± 0.62 |
| 45° ridge (L = 78 µm) | −4.08 ± 0.68 | −10.82 ± 1.63 | −11.2 ± 1.48 | N/A | 7.52 ± 0.54 |
| 30° ridge (L = 200 µm) | −4.11 ± 1.75 | −11.2 ± 2.91 | −11.6 ± 2.01 | N/A | 11.1 ± 0.51 |

| 7.5 µm particle lateral displacement per ridge (µm) | | |
| --- | --- | --- |
| Channel design | Ridge | Between ridge |
| 30° ridge (L = 100 µm) | −12.0 ± 0.79 | 10.4 ± 1.05 |
| 45° ridge (L = 78 µm) | −13.3 ± 1.15 | 12.4 ± 1.82 |
| 30° ridge (L = 200 µm) | −14.7 ± 1.61 | 14.1 ± 2.52 |

Figure 4C:
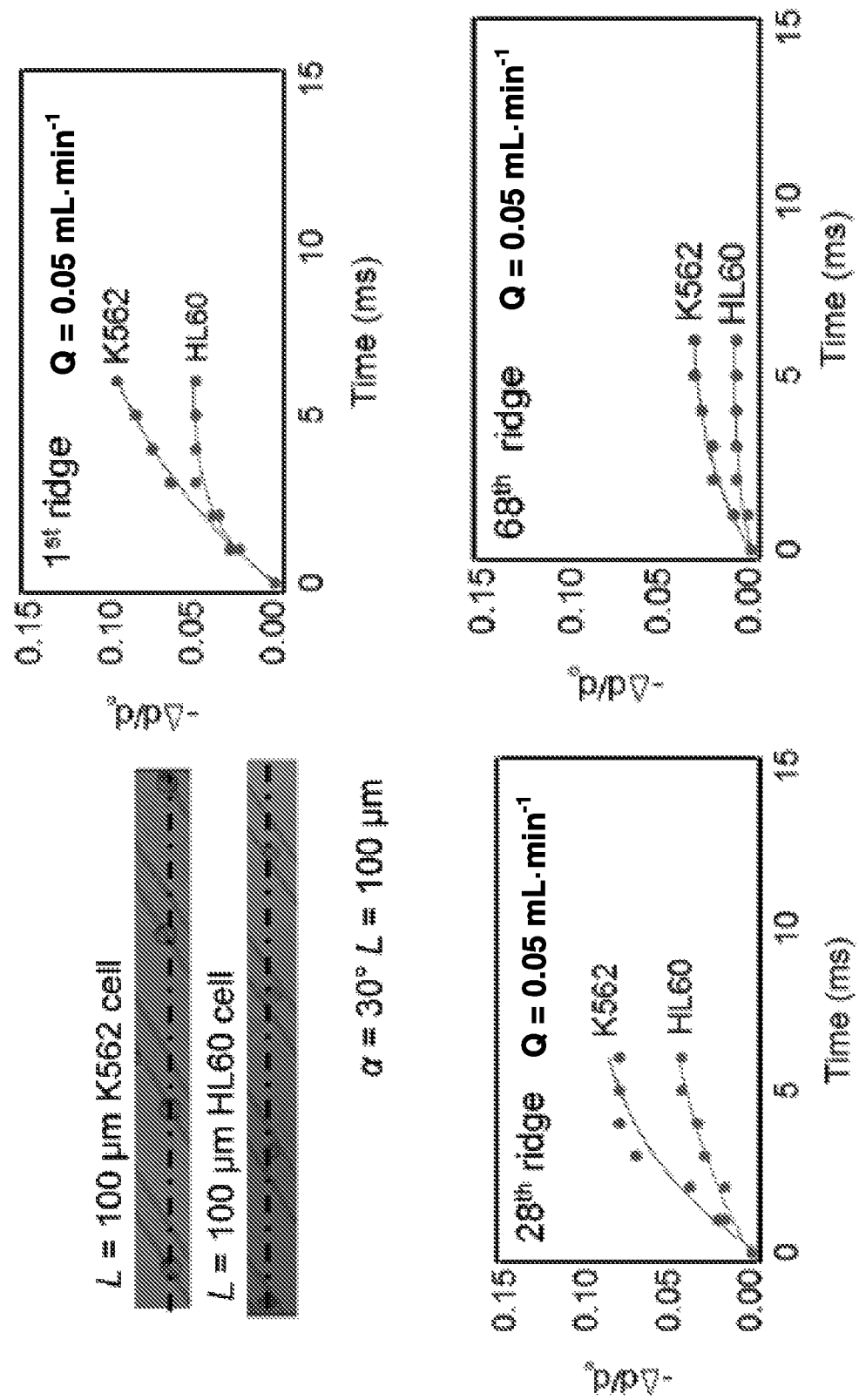
Figure 4E:
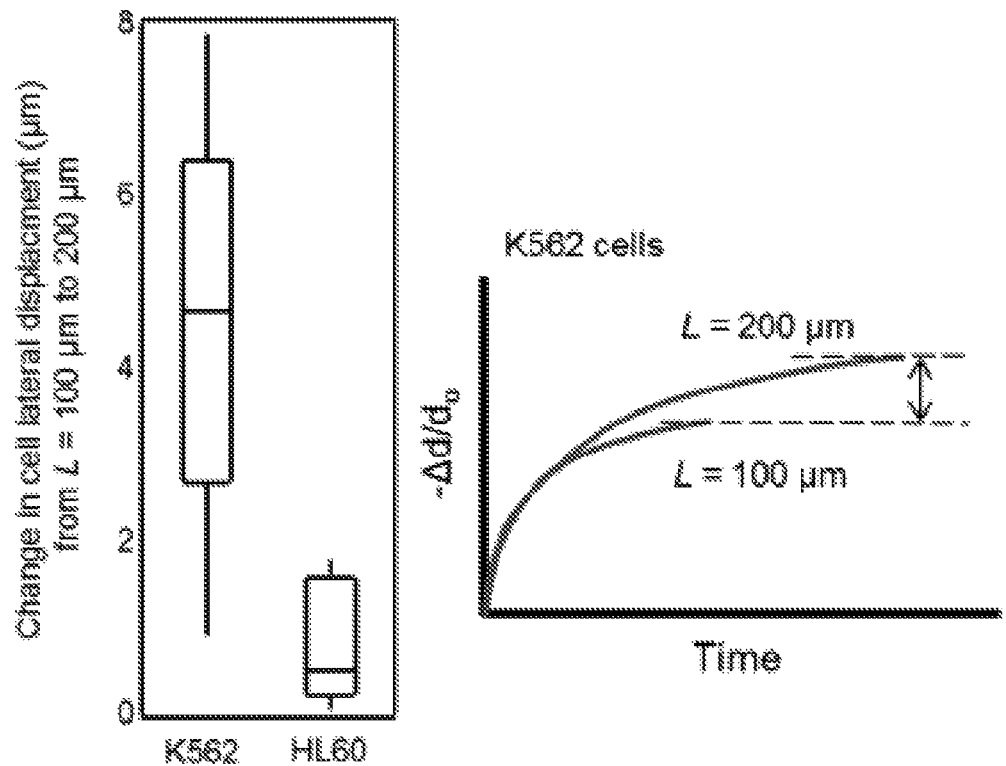
FIGS. 4e and 4f illustrate the effects of larger spacing between ridges and reducing channel flow rate on cell relaxation, in accordance with an exemplary embodiment of the present disclosure.
Figure 4F:
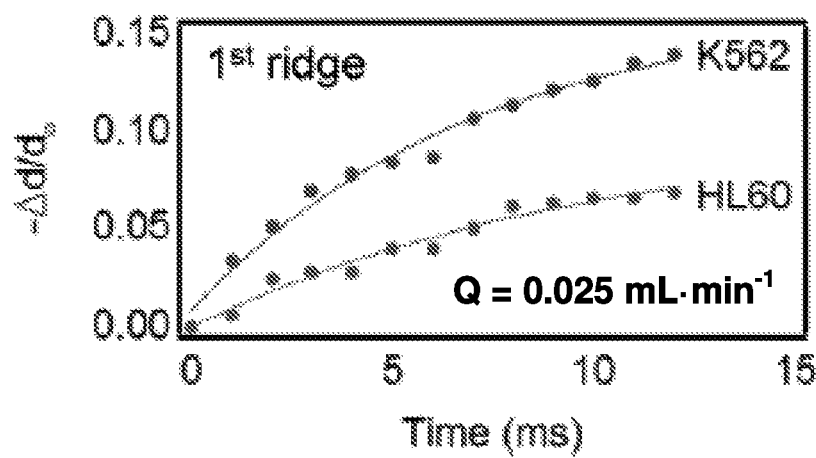

Increasing the ridge spacing (L), resulted in increased relaxation of weakly viscous cells, which could be used to separate cells viscoelastically. Cell relaxation can be measured by recording the apparent diameter of the compressed cells between first ridge and second ridge in a 9 µm gap channel (h=9 µm, L=100 µm and 200 µm) for both weakly viscous K562 and highly viscous HL60 cells. In both cases, the less viscous K562 cells relaxed more quickly than HL60 cells, in agreement with the AFM measurements, as shown in FIGS. 4c and 4d. In addition, the increased ridge spacing may allow both cell types a longer duration to relax between compressions amplifying the difference in relaxation between the K562 and HL60 cells (FIG. 4e). The additional relaxation resulted from changing the ridge spacing from L=100 µm to 200 µm is shown for K562 cells in FIG. 4e. Moreover, the additional relaxation increased K562 cell lateral displacement, but the effect was more significant than for HL60 cells (FIG. 4e). Therefore, the increased ridge spacing did not result in appreciable cell relaxation of the highly viscous HL60 cells. As a result, the increased ridge spacing enhanced the divergency of lateral displacement between K562 and HL60 cells.

Another parameter that can affect cell trajectory is the ridge angle. When the ridge angle is more aligned with the channel axis (smaller α), elastic cells tend to roll at the leading edge of the ridges. K562 cells display more positive lateral displacement at the first ridge when the ridge is at 30° compared to 45° as evidenced in Table 1. Unlike K562 cells, the ridge angle did not strongly affect viscous HL60 cell trajectory because HL60 cells remained deformed and had little contact with the ridges.

For both K562 and HL60 cells, repeated compressions result in negative lateral displacement after 10 ridges as evidenced in Table 1. A possible mechanism for this observed behavior could be that cell relaxation is a time dependent dynamic response to such periodic compression. As such the change in cell viscoelastic behavior in the channel could be attributed to alteration of the cytoskeleton, possibly by disassembly of stress fiber networks or buckling and disintegration of stress fibers.

The channel flow rate can also be used to affect cell trajectory. In one case, reducing the flow rate to Q=0.025 mL per minute from Q=0.05 mL per min led to cells having similar relaxation in L=100 μm channel compared to L=200 μm channel at 0.05 mL per minute (FIG. 4e). While a higher flow rate can increase throughput, viscoelastic separation can be negatively impacted by flow rates which result in insufficient cell relaxation. Preferably a flow rate of 0.05 mL per minute may be used to produce sufficient differential relaxation and cell sorting of HL60 and K562 cells.

As cells undergo initial compression, the cell trajectory is dominated by size-adjusted elasticity. However, as cell progress through the channel and rapidly compressed by sequential ridges, cell viscosity which sets cell relaxation time plays a more important role. When cell relaxation time is much longer than the time between compressions, the deformed cells are in disc-shape and their trajectory is primarily affected by the secondary flow induced by the diagonal ridges. Thus, cell size, cell stiffness and cell relaxation can be used to design microfluidic channels to sort cells primarily based on cell viscous properties.

Cell Enrichment of K562 and HL60

The K562 and HL60 cell lateral displacement and pair-wise separation results are summarized in Table 1 and Table 2 respectively. Additionally flow cytometry was used to verify the improvement in cell separation and derive a cell enrichment factor. The cell enrichment factor normalizes the separated cell populations with the initial cell mixture to obtain enrichment. The HL60 enrichment factor is set forth in equation 3.

$$c.e.f._{HL60} = \frac{(HL60/K526)_{HL60\ outlet}}{(HL60/K526)_{initial\ mixture\ inlet}} \quad (Eq.\ 3)$$

TABLE 2

| Channel Design | Cell Enrichment Factor | |
|---|---|---|
| | K562 | HL60 |
| 30° ridge; L = 100 μm, 30 ridges | 3.26 | 2.29 |
| 45° ridge; L = 78 μm, 30 ridges | 2.07 | 2.85 |

TABLE 2-continued

| Channel Design | Cell Enrichment Factor | |
|---|---|---|
| | K562 | HL60 |
| 30° ridge; L = 100 μm, 70 ridges | 1.15 | 1.75 |
| 30° ridge; L = 200 μm, 30 ridges | 6.34 | 4.04 |

Cell separation of HL60 and K562 mixtures was compared using two channel designs. The channel with ridge spacing L=200 μm had a cell enrichment factor of 6.34 and 4.04 for K562 and HL60 cells respectively. Compared to L=100 μm, the enrichment was improved by more than 90% for K562 and 75% for HL60. Cell enrichment data for other these and other channel designs are summarized in Table 2.

Cell Enrichment of K562 and Healthy Leukocytes

Figure 5A:
FIG. 5a shows a flow cytometric analysis of cell enrichment for an embodiment comprising a 30 degree ridge angle and a ridge spacing of 100 µm, in accordance with an exemplary embodiment of the present disclosure.
Figure 5B:
FIG. 5b shows a flow cytometric analysis of cell enrichment for an embodiment comprising a ridge spacing of 200 µm, in accordance with an exemplary embodiment of the present disclosure.
Figure 7A:
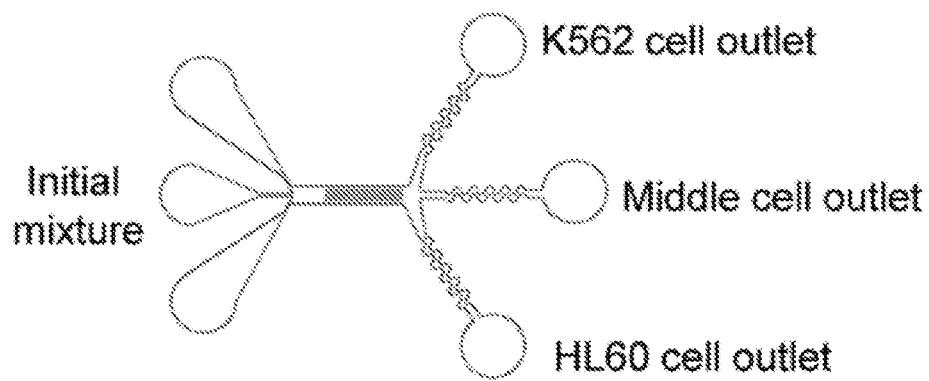
FIG. 7f shows a flow cytometric analysis of cell fractionation using a three-outlet microfluidic device, in accordance with embodiments of the present disclosure.
Figure 7B:
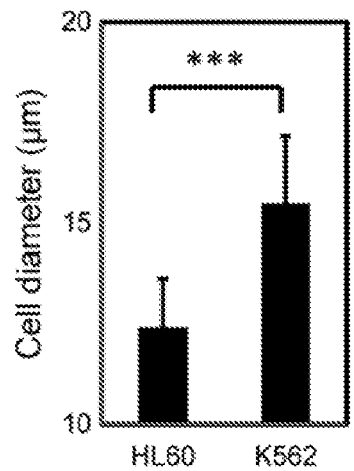
Figure 7C:
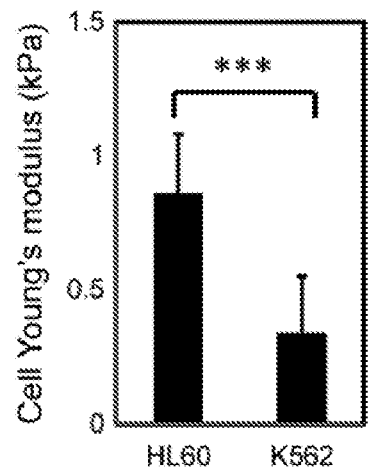
Figure 7D:
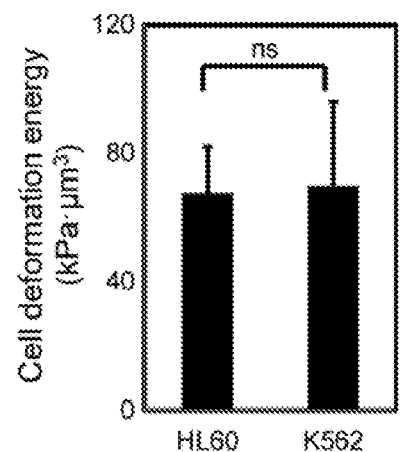
Figure 7E:
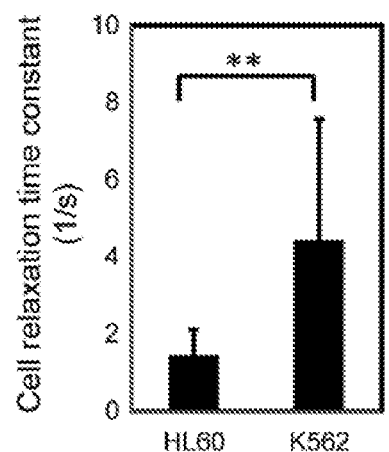
Figure 7F:
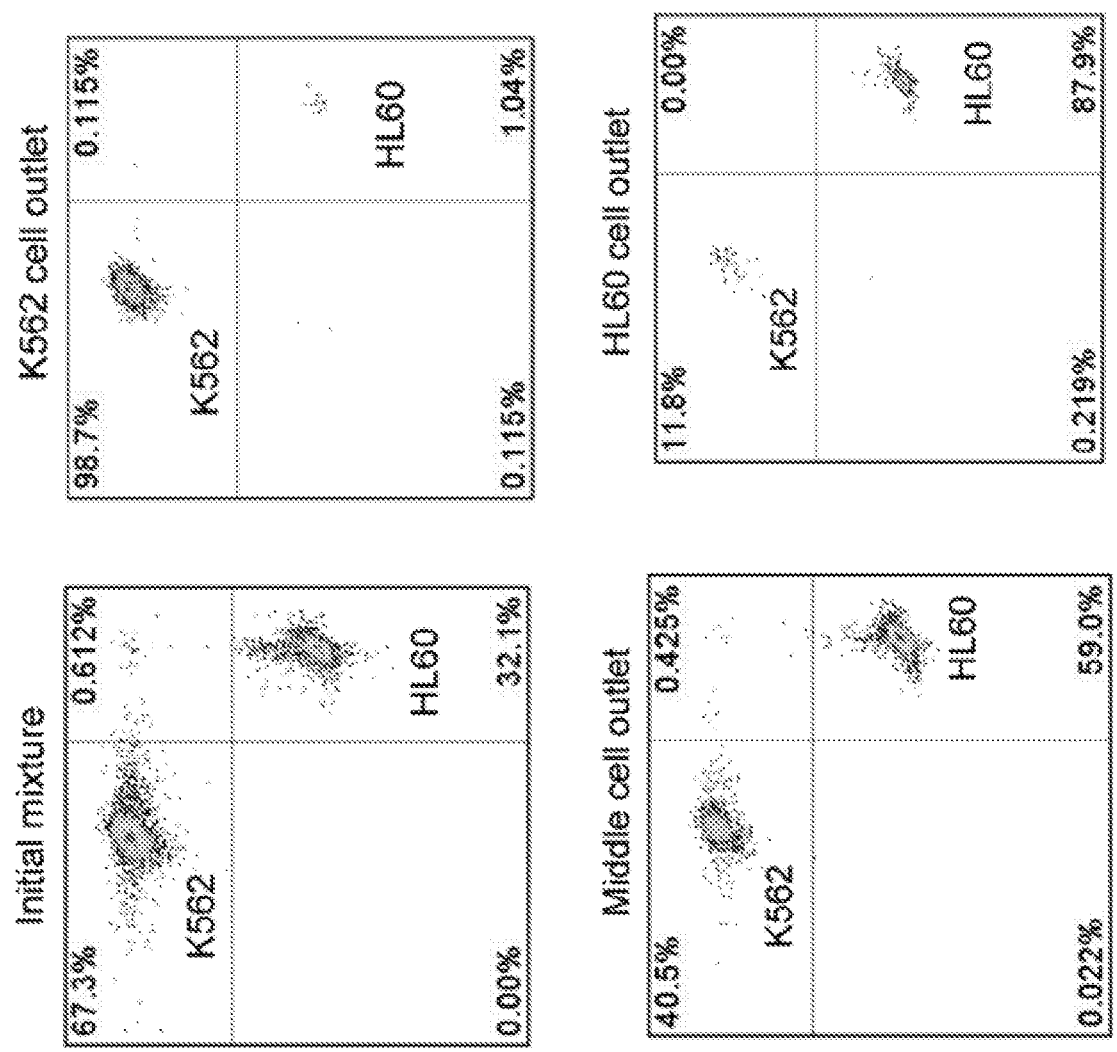

Application of this microfluidic approach to other cell lines is envisioned, and was further demonstrated to enrich K562 leukemia cell from healthy white blood cells. The white blood cells (WBC) were isolated from whole blood of healthy adults and suspended in saline solution. AFM microscopy was used to measure the white blood cell stiffness and relaxation time constant. Cell diameter of WBC population is smaller than the K562 cells (FIG. 5a). The WBC have higher Young's modulus (FIG. 5b). K562 cells have higher size-adjusted elasticity (deformation energy) primarily due to large cell diameter since it scales to the quartic power (FIG. 5c). Similar to HL60, the WBC are highly viscous cells (FIG. 5d). Coefficients of variation of cell size, stiffness and viscosity distributions are more pronounced, which could be a result of WBC population consisting of multiple cell types.

Using a channel design (α=30°, L=200 μm, 30 ridges), flow cytometric analysis indicated a 5.3 fold K562 enrichment (FIG. 5e). WBC display lower size-adjusted elasticity and similar viscosity compared to HL60 cells. Further testing using alternative channel designs was also performed.

Example 2—Device for Cell Separation and Fractionation

Two types of leukemia cell lines: K562 and HL60 may be sorted using a device incorporating three outlet channels. The biomechanical properties of these two cell types and the results of cell separation using a binary output channel have been characterized. Additionally, the cell size, Young's modulus, size-adjusted elasticity (deformation energy) and the relaxation rate constants are given (FIG. 6a-d). The average cell diameter for K562 and HL60 cells is 15.5±1.7 μm (n=114) and 12.4±1.2 μm (n=36). AFM measurements of cells' Young's moduli show that HL60 (E=0.86±0.22 kPa, n=24) is stiffer than K562 (E=0.34±0.21 kPa, n=114). The average values of Young's modulus and cell diameter are used to calculate cell deformation energy. K562 and HL60 have similar deformation energy (69.8±26.1, and 67.6±14.5 kPa μm$^3$, respectively) when compressed with 9-μm channel gap height. AFM measurements of cell relaxation show HL60 (1.45±0.65 s$^{-1}$, n=30) is slower in size recovery than K562 (4.42±3.15 s$^{-1}$, n=52). t test was used to analyze statistical significance: p<0.001, *p<0.0001 and ns no significance. The size-adjusted elasticity accounts for cell size and cell stiffness as a single parameter.

K562 and HL60 cells are primarily sorted based on differences in cell relaxation due to a higher viscosity of HL60 cells. Cell mixtures are labeled fluorescently and mixed at 1-2 million cells per mL. The flow rate ranges from 0.0125 to 0.025 mL per min. The cell sorting result with the cell fractionation is evaluated by flow cytometry. Flow cytometric analysis of cell enrichment was assessed using a three-outlet channel. At the outlets, the cell enrichment factor for K562 and HL60 cells is 45.3 and 15.6, respectively. The purity of enriched K562 cells and HL60 cells is 98.7 and 87.9%, respectively. The total number of cells initially is 22,000. The number of cells in the K562 outlet, the middle outlet and the HL60 outlet is 11,500, 4600, and 2100, respectively, and rounded the nearest hundred. To quantify cell sorting efficiency, the cell enrichment factor (Equation 3) can be used. The cell enrichment factor accounts cell enrichment by normalizing ratios of cell proportions at outlets to the original cell proportion in the initial mixture.

For the three-outlet device, the cell enrichment factor for K562 and HL60 cells is 45.3 and 15.6, respectively. The fractionation improves the cell enrichment factor by an order of magnitude compared to the results utilizing binary outlets. The additional outlet in the middle collects those K562 and HL60 cells that have overlapping biomechanical properties. Therefore, the three-outlet channel enables a dramatic improvement in cell sorting purity.

In addition to enrichment of cell mixtures into individual cell types, the three-outlet channel can also be applied to fractionate a single cell type into distinct biomechanical phenotypes. Since biological cells are inherently heterogeneous in nature, their biomechanical properties may include large variations due to differences in cytoskeleton or nucleus. For example, K562 cells have average Young's modulus 0.34 kPa and a standard deviation 0.21 kPa. Utilizing the fractionation approach, we are able to obtain subpopulations of K562 cells with differing biomechanical properties.

K562 cells were fractionated using the three-outlet channel (outlet A, B, and C), and the separated cells were characterized with AFM and optical microscopy immediately after collection. The biomechanical properties of the K562 cells at inlet are characterized. Atomic force microscopy measurements of cell Young's modulus show that sorted K562 cells have different average Young's modulus outlet A (E=0.47±0.21 kPa, n=27), outlet B (E=0.33±0.24 kPa, n=53), and outlet C (E=0.25±0.098 kPa, n=38). The average Young's modulus at the inlet is 0.39±0.21 kPa (n=110). Spearman's correlation analysis of the separated cells produces a p value of 0 and an r value of −0.42. Cell sizes are different at three outlets with the largest average cell diameter in outlet A and the smallest average cell diameter in outlet C. The cell diameters in outlet A, B, C and inlet are 16.28±1.4 μm (n=27), 15.42±1.78 μm (n=53), 14.98±1.56 μm (n=38) and 15.2±1.2 μm (n=110), respectively. Spearman's correlation analysis of the separated cells produces a p value of 0.001 and a r value of −0.29. These data show that K562 cells can be successfully separated into three populations with different biomechanical properties, predominantly stiffness and size, but not significantly by cell relaxation. The size-adjusted elasticity (deformation energy) that combines the effects of cell size and stiffness is also significantly different between the cells collected at three outlets.

EMBODIMENTS

Additionally or alternatively, the disclosure can include one or more of the following embodiments.

Embodiment 1

A microfluidic device comprising one or more inlets; a first wall and a second wall, the walls being substantially planar to each other and the first wall having a plurality of ridges wherein each ridge of the plurality of ridges protrudes normal to the first wall and defines a compression gap between the ridge and a surface of the second wall; and two or more outlets; wherein each ridge of the plurality of ridges is diagonally oriented with respect to a central axis of the microfluidic device and each respective ridge of the plurality of ridges is separated by a ridge spacing.

Embodiment 2

A cell sorting device for sorting a plurality of cells based on one or more biophysical cellular properties including size, elasticity, viscosity, and/or viscoelasticity, the cell sorting device comprising an inlet for flowing a cell medium comprising the plurality of cells into the device at a flow velocity; a top planar wall and a bottom planar wall wherein the top planar wall comprises a plurality of ridges protruding normal to the top planar wall and defining a compression gap between a surface of the bottom planar wall and each ridge of the plurality of ridges; and a plurality of outlets for collecting sorted portions of the plurality of cells wherein the sorted portions share one or more biophysical properties; wherein each ridge of the plurality of ridges is oriented diagonally with respect to a central flow axis and each respective ridge of the plurality of ridges is separated by a diagonally-oriented ridge spacing.

Embodiment 3

A method for sorting a plurality of cells using a microfluidic device, the method including the steps of providing a cell medium, the cell medium comprising the plurality of the cells to be sorted, passing the cell medium through a microchannel having a plurality of diagonally-oriented ridges; and collecting sorted portions of the cell medium at two or more collection points. The plurality of diagonally-oriented ridges define a compression gap between a bottom surface of the microchannel and each ridge of the plurality of ridges. When the cell medium passes through the microchannel, at least a portion of the plurality of cells can undergo one or more compressions due to the compression gap.

Embodiment 4

The methods or devices of one of the previous embodiments, wherein the height of the compression gap is about 4 to about 16 microns, is about 5 to about 14 microns, or is about 6 to about 11 microns.

Embodiment 5

The methods or devices of one of the previous embodiments wherein the width of the ridge spacing is about 50 to about 350 microns, about 100 to about 300 microns, about 100 to about 200 microns, or about 100 microns or less.

Embodiment 6

The methods or devices of one of the previous embodiments wherein the width of the ridge spacing is about 100 to about 200 microns and a ridge angle formed by at least one ridge with respect to the central axis of the microfluidic device is about 30 degrees; or wherein the width of the ridge spacing is about 100 microns or less and a ridge angle formed by at least one ridge with respect to the central axis of the microfluidic device is about 45 degrees.

Embodiment 7

The methods or devices of one of the previous embodiments wherein a ridge angle formed by at least one ridge with respect to the central axis of the microfluidic device is about 20 to about 75 degrees; or wherein a ridge angle formed by at least one ridge with respect to the central axis of the microfluidic device is about 30 to about 60 degrees.

Embodiment 8

The methods or devices of one of the previous embodiments wherein the plurality of ridges comprises at least 7 ridges, 7 to 21 ridges, or 14 ridges.

Embodiment 9

The methods or devices of one of the previous embodiments comprising two outlets, at least two outlets, three outlets, at least three outlets, five outlets, or at least five outlets.

Embodiment 10

The methods or devices of one of the previous embodiments further comprising an expansion region downstream from the plurality of ridges.

Embodiment 11

The methods or devices of one of the previous embodiments wherein at least one outlet comprises a flow apportionment region, a flow balancing region, and a collection point.

Embodiment 12

The methods or devices of one of the previous embodiments wherein at least one outlet comprises a flow apportionment region that is a different size than at least a second flow apportionment region.

Embodiment 13

The methods or devices of one of the previous embodiments wherein at least one collection point is downstream from a flow balancing region and a flow apportionment region.

Embodiment 14

The methods or devices of one of the previous embodiments wherein at least one outlet comprises a flow balancing region that is a serpentine channel.

Embodiment 15

The methods or devices of one of the previous embodiments wherein the width of the ridge spacing is about 200 microns, a ridge angle formed by at least one ridge with respect to the central axis of the microfluidic device is about 30 degrees, and the plurality of ridges comprises 30 ridges.

Embodiment 16

The methods or devices of one of the previous embodiments wherein the flow velocity is about 3 to about 1000 mm/s.

Embodiment 17

The methods or devices of one of the previous embodiments wherein the width of the ridge spacing is about 100 to about 300 microns and the predetermined flow velocity is about 3 to about 1000 mm/s.

Embodiment 18

The methods or devices of one of the previous embodiments wherein the width of the ridge spacing is about 100 to about 300 microns, the flow velocity is about 3 to about 1000 mm/s, and a ridge angle formed by at least one ridge with respect to the central flow axis is about 20 to about 75 degrees.

Embodiment 19

The methods or devices of one of the previous embodiments further comprising one or more sheath flow inlets for flowing a sheath fluid into the cell sorting device.

Embodiment 20

The methods or devices of one of the previous embodiments wherein the height of the compression gap is smaller than an average cell diameter.

Embodiment 21

The methods or devices of one of the previous embodiments wherein the cell medium comprises at least a first cell portion that is more viscous than at least a second cell portion, wherein the more viscous cell portion follows a different trajectory from the less viscous cell portion.

Embodiment 22

The methods or devices of one of the previous embodiments the cell medium comprises at least a first cell portion that is more viscous than at least a second cell portion, wherein the more viscous cell portion follows a different trajectory from the less viscous cell portion, and the more viscous cell portion is collected at a first outlet and the less viscous cell portion is collected at a second outlet.

Embodiment 23

The methods or devices of one of the previous embodiments wherein at least one outlet comprises a collection point and a more viscous cell portion is collected at a first collection point and a less viscous cell portion is collected at a second collection point.

Embodiment 24

The methods or devices of one of the previous embodiments wherein collecting sorted portions of the cell medium occurs at two collection points; or wherein collecting sorted portions of the cell medium occurs at three collection points.

Embodiment 25

The methods or devices of one of the previous embodiments wherein the device or microchannel comprises at least two trajectories for the plurality of cells at each ridge.

Embodiment 26

The methods or devices of one of the previous embodiments wherein at least a portion of the plurality of cells undergoes one or more compressions due to the compression gap.

Embodiment 27

The methods or devices of one of the previous embodiments wherein a cell trajectory through the microchannel or device is determined by a characteristic of the cell selected from cell size, stiffness, relaxation time, viscosity, or elasticity, and combinations thereof.

Embodiment 28

The methods or devices of one of the previous embodiments wherein the cells undergo a compression of about 25 to about 75% of the average diameter of the cells.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily utilized as a basis for the design of other structures, methods, and systems for carrying out the several purposes of the embodiments and claims presented in this application. It is important, therefore, that the claims be regarded as including such equivalent constructions.

We claim:

1. A microfluidic device comprising:
a first wall;
a second wall;
first and second side walls, each extending between the first wall and the second wall and with the first and second walls, forming a channel;
a plurality of ridges, wherein each ridge of the plurality of ridges extends into the channel normal from the first wall and defines a compression gap between the ridge and the second wall;
an inlet for inletting fluid into the channel;
an outlet for outletting fluid from the channel; and
an expansion region disposed downstream from the plurality of ridges;
wherein each ridge of the plurality of ridges is diagonally oriented with respect to a central axis of the microfluidic device; and
wherein each pair of adjacent ridges of the plurality of ridges is separated by a ridge spacing having a width of at least 100 microns.

2. The microfluidic device of claim 1, wherein a height of each of the compression gaps is from about 4 microns to about 16 microns.

3. The microfluidic device of claim 1, wherein the width of each of the ridge spacings is from about 100 microns to about 300 microns.

4. The microfluidic device of claim 1, wherein the width of each of the ridge spacings is from about 100 microns to about 200 microns and a ridge angle formed by at least one ridge with respect to the central axis of the microfluidic device is about 30 degrees.

5. The microfluidic device of claim 1, wherein a ridge angle formed by at least one ridge with respect to the central axis of the microfluidic device is from about 20 to about 75 degrees.

6. The microfluidic device of claim 1, wherein the plurality of ridges comprises from 7 to 21 ridges.

7. A microfluidic device comprising:
a first wall;
a second wall;
first and second side walls, each extending between the first wall and the second wall and with the first and second walls, forming a channel;
a plurality of ridges, wherein each ridge of the plurality of ridges extends into the channel normal from the first wall and defines a compression gap between the ridge and the second wall;
an inlet for inletting fluid into the channel;
an outlet for outletting fluid from the channel; and
wherein the outlet comprises a flow apportionment region, a flow balancing region, and a collection point;
wherein each ridge of the plurality of ridges is diagonally oriented with respect to a central axis of the microfluidic device; and
wherein each pair of adjacent ridges of the plurality of ridges is separated by a ridge spacing having a width of at least 100 microns.

8. The microfluidic device of claim 7, wherein the flow balancing region comprises a serpentine channel.

9. A method for sorting cells using a microfluidic device comprising:
providing a cell medium to a microfluidic device comprising:
a first wall;
a second wall;
first and second side walls, each extending between the first wall and the second wall;
a plurality of ridges, wherein each ridge of the plurality of ridges extends normal from the first wall toward the second wall, and defines a compression gap between the ridge and the second wall; and
an expansion region disposed downstream from the plurality of ridges;
wherein each ridge of the plurality of ridges is diagonally oriented with respect to a central axis of the microfluidic device;
passing the cell medium through the microfluidic device; and
collecting sorted portions of the cell medium downstream the expansion region;
wherein at least a portion of cells undergo one or more compressions due to the compression gaps.

10. The method of claim 9, wherein the cell medium comprises a first cell portion and a second cell portion;

wherein the first cell portion has a higher viscosity than the second cell portion;

wherein the microfluidic device comprises two outlets, a first outlet and a second outlet; and wherein the first cell portion is collected downstream the first outlet and the second cell portion is collected downstream the second outlet.

11. The method of claim 9, wherein each pair of adjacent ridges of the plurality of ridges is separated by a ridge spacing.

12. The method of claim 11, wherein the widths of each of the ridge spacings has a width from about 100 microns to about 350 microns.

13. The method of claim 12, wherein a ridge angle formed by at least one ridge with respect to a central flow axis of the microfluidic device is from about 20 degrees to about 75 degrees.

14. The method of claim 10, wherein the first cell portion is collected at a first collection point and the second cell portion is collected a second collection point; and wherein at least one collection point is downstream from a flow balancing region and a flow apportionment region of the microfluidic device.

15. The method of claim 9, wherein a height of each of the compression gaps is from about 4 microns to about 16 microns.

16. The method of claim 9, wherein the plurality of ridges comprises from 7 ridges to 21 ridges.

17. The microfluidic device of claim 7, wherein a height of each of the compression gaps is from about 4 microns to about 16 microns.

18. The microfluidic device of claim 7, wherein a ridge angle formed by at least one ridge with respect to the central axis of the microfluidic device is from about 20 to about 75 degrees.

19. A microfluidic device comprising:
a first wall and a second wall, forming therebetween a path for fluid flow;
a set of ridges extending into the path between the first wall and a second wall;
an inlet for supplying a fluid flow to the path between the first wall and a second wall;
an outlet for removing a fluid flow from the path between the first wall and a second wall; and
an expansion region disposed upstream from the outlet and downstream from the set of ridges; and
wherein each ridge:
extends a ridge distance into the path between the first wall and a second wall, each ridge distance being less than the distance between the first wall and a second wall, such that each ridge extends from one of the first and second walls towards the other of the first and second walls and forms a compression gap between the ridge and the other of the first and second walls toward which the ridge extends;
is diagonally oriented at a ridge angle with respect to a central axis of the microfluidic device; and
is separated from another ridge by a ridge spacing.

20. The microfluidic device of claim 19, wherein each ridge of the set of ridges extends from the same wall.

21. The microfluidic device of claim 19, wherein a height of each compression gap is the same.

22. The microfluidic device of claim 19, wherein each ridge spacing is from about 100 microns to about 200 microns;
wherein each ridge angle is from about 20 degrees to about 75 degrees; and
wherein a height of each of the compression gaps is from about 4 microns to about 16 microns.

23. The microfluidic device of claim 19, wherein the outlet comprises a flow apportionment region, a flow balancing region, and a collection point.

* * * * *